(12) United States Patent
Carola et al.

(10) Patent No.: US 7,943,662 B2
(45) Date of Patent: May 17, 2011

(54) FLAVONOID COMPLEXES

(75) Inventors: Christophe Carola, Heidelberg (DE); Anne Toullec, Antony (FR); Herwig Buchholz, Frankfurt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 895 days.

(21) Appl. No.: 11/791,544

(22) PCT Filed: Nov. 3, 2005

(86) PCT No.: PCT/EP2005/011738
§ 371 (c)(1),
(2), (4) Date: May 24, 2007

(87) PCT Pub. No.: WO2006/056297
PCT Pub. Date: Jun. 1, 2006

(65) Prior Publication Data
US 2008/0112905 A1 May 15, 2008

(30) Foreign Application Priority Data
Nov. 25, 2004 (DE) .......................... 10 2004 056 900

(51) Int. Cl.
*A61K 31/353* (2006.01)
*A61K 31/724* (2006.01)
(52) U.S. Cl. .......................................... 514/456; 514/58
(58) Field of Classification Search ........................ None
See application file for complete search history.

(56) References Cited

U.S. PATENT DOCUMENTS

| 7,128,900 B2 | 10/2006 | Buchholz et al. |
| 2004/0081675 A1 | 4/2004 | Wirth et al. |

FOREIGN PATENT DOCUMENTS

| EP | 1 382 329 A | | 1/2004 |
| JP | 11-169148 | * | 6/1999 |
| WO | WO 02/069926 A | | 9/2002 |
| WO | WO 2005/068484 A | | 7/2006 |

OTHER PUBLICATIONS

Haiyun, D. "Preparation and spectral investigation . . ." Spectrochim. Acta part A (2003) vol. 59, pp. 3421-3429.*
Wang, X. et al "Thin layer chromatographic study on inclusion complex . . ." Anal. Lett. (2001) vol. 34, No. 2, pp. 239-245.*
Caplus abstract of Muranishi et al JP 11-169148 (1999).*
Loftsson T. et al., Cylodextrins in Topical Drug Formulation Theory and Practice, International Journal of Pharmaceutics, Aug. 2001, pp. 15-30, 225(1/2).
Miyake et al., Improvement of Solubility and Oral Bioavailability of Rutin by Complextion with 2-Hydroxypropyl-β-cyclodextrin, Pharmaceuticla Development and Technology, 2002, 5(3), pp. 399-407, Marcel Dekker, Inc.
Nguyen et al., Study of Inclusion Compounds of Rutin, Congr. Int. Technology, Pharm 6th, 1992, Vo. 5, pp. 408-416.
Dimova et al., Safety-Assessment of 3-Methoxyquercetin as an Antirhinoviral compound for Nasal Application Effect on Ciliary Beat Frequency, International Journal of Pharmaceutics, 2003, pp. 95-103, 263 , Elsevier B. V.
Ficarra et al, Study of Flavonoids/β-Cyclodextrins Inclusion Complexes by NMR, FT-IR, DSC, X-ray Investigation, Journal of Pharmaceutical and Biomedical Analysis, 2002, pp. 1005-1014, 29, Elsevier Science B.V.

(Continued)

*Primary Examiner* — Leigh C Maier
(74) *Attorney, Agent, or Firm* — Millen, White, Zelano & Branigan, P.C.

(57) ABSTRACT

The invention relates to complexes of certain flavonoid derivatives, of the formula (I), where $R^1$ and $R^2$ are selected from H and $OR^{11}$, where $OR^{11}$ stands, independently of one another, for OH, straight-chain or branched $C_1$- to $C_{20}$-alkoxy groups, straight-chain or branched $C_3$- to $C_{20}$-alkenyloxy groups, straight-chain or branched $C_1$- to $C_{20}$-hydroxyalkoxy groups, where the hydroxyl group(s) may be bonded to a primary or secondary carbon atom in the chain and furthermore the alkyl chain may also be interrupted by oxygen, and/or $C_3$- to $C_{10}$-cycloalkoxy groups and/or $C_3$- to $C_{12}$-cycloalkenyloxy groups, where the rings may in each case also be bridged by —$(CH_2)_n$— groups, where n=1 to 3, and/or mono- and/or oligoglycosyl radicals, with the proviso that at least one radical from $R^1$ and $R^2$ stands for $OR^{11}$, and $R^3$ to $R^{10}$ may be identical or different and stand, independently of one another, for radicals which are substantially inert with respect to the UV properties, to compositions which comprise such complexes, to corresponding processes for the preparation of the complexes or the compositions comprising the latter, and to the use thereof, in particular for the care, preservation or improvement of the general condition of the skin or hair and for light protection.

21 Claims, No Drawings

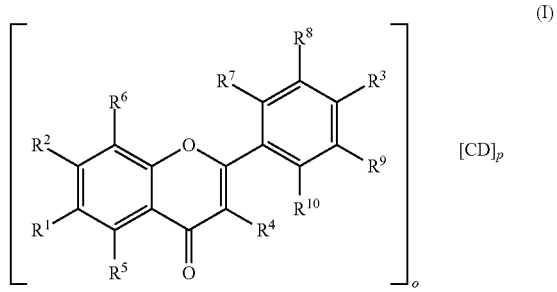

OTHER PUBLICATIONS

Yingyong Huaxue, Chinese Journal of Applied Chemistry, 2002, pp. 702-704, 19(7).

Hostettmann, A Study of the Cyclodextrin Complexes of Flavonoids and Azodynes by Thin Layer Chromatography. Part II. Hydroxypropylcyclodextrins, Photochemical Analysis, 2002, pp. 380-382, 11, John Wiley & Sons, Ltd.

Buschmann H-J et al., Applications of Cyclodextrins in Cosmetic Products: A Review, Journal of Cosmetic Science, (May 2002), pp. 185-191, 53(3), Society of Cosmetic Chemists, NY, NY.

Patent Abstract of Japan—Publication No. 11-169148—Date of Publication of application: Jun. 29, 1999—Ogawa Koryo Co Ltd., "Suppressant for Flavor Deterioration".

* cited by examiner

FLAVONOID COMPLEXES

The invention relates to complexes of certain flavonoid derivatives, to compositions which comprise such complexes, to corresponding processes for the preparation of the flavonoid derivatives or the compositions comprising same, and to the use thereof, in particular for the care, preservation or improvement of the general condition of the skin or hair and for light protection.

A certain degree of tanning of the skin is regarded in morn society as attractive and as an expression of vigour and sportiness. In addition to this desired action of the sun on the skin, a number of undesired side effects occur, such as sunburn or premature skin ageing and wrinkling. A number of effective UV filters have now been developed which, applied to the skin in the form of creams, lotions or gels, are able effectively to prevent the development of sunburn, even in the case of relatively great exposure to the sun. The UV filters present in the pharmaceutical or cosmetic composition form a film or layer on the surface of the skin and do not penetrate into deeper skin layers with further care substances present in the composition. Known UV filters and sunscreens thus only act by absorbing certain regions of the sunlight, thus preventing this radiation from penetrating into deeper layers of the skin. As is known, the most dangerous part of solar radiation is formed by ultraviolet rays having a wavelength of less than 400 nm. The lower limit for the ultraviolet rays which reach the earth's surface is restricted to about 280 nm by absorption in the ozone layer. The sun-protection filters usual today in cosmetics absorb in a wavelength range from 280 to 400 nm. This range covers UV-B rays having a wavelength of between 280 and 320 nm, which play a crucial role in the formation of solar erythema, and also UV-A rays having a wavelength of between 320 and 400 nm, which tan the skin, but also allow ageing, favour the triggering of an erythematous reaction or can exacerbate this reaction in certain people or even trigger phototoxic or photoallergic and irritative reactions.

Skin damage is not caused just by sunlight, but also by other external influences, such as cold or heat. Furthermore, the skin undergoes natural ageing, with the formation of wrinkles and a reduction in the elasticity of the skin.

The object of care cosmetics is wherever possible to obtain the impression of youthful skin. In principle, there are various ways of achieving this object. For example, existing skin damage, such as irregular pigmentation or the development of wrinkles, can be compensated for by covering powders or creams. Another approach is to protect the skin against environmental influences which lead to permanent damage and thus ageing of the skin. The idea is therefore to intervene in a preventative manner and thus to delay the ageing process. One example of this is the UV filters already mentioned, which, as a result of absorption of certain wavelength ranges, prevent or at least reduce skin damage. Whereas in the case of UV filters the damaging event, the UV radiation, is screened off by the skin, another route involves attempting to support the skin's natural defence or repair mechanisms against the damaging event. Finally, a further approach involves compensating for the weakening defence functions of the skin against harmful influences with increasing age by externally supplying substances which are able to replace this diminishing defence or repair function. For example, the skin has the ability to scavenge free radicals formed by external or internal stress factors. This ability diminishes with increasing age, causing the ageing process to accelerate with increasing age.

A further difficulty in the preparation of cosmetics is that active ingredients which are intended to be incorporated into cosmetic compositions are frequently unstable and may be damaged in the composition. The damage may be caused, for example, by a reaction with atmospheric oxygen or by absorption of UV rays. The molecules damaged in this way may, for example, change their colour and/or lose their activity through their structural change.

DE 195 08 608 A1 describes a light-stable cosmetic composition. Cosmetic compositions are disclosed for protection against UV rays having a wavelength of between 280 and 400 nm which comprise at least one tetraalkylquercetin in a cosmetically acceptable, oil-based medium.

DE 197 55 504 A1 describes the use of flavones and flavonoids against UV-induced decomposition of dibenzoylmethane and its derivatives.

WO 02/00214 describes the use of certain flavone derivatives for the preparation of oral medicaments for the systemic treatment and prophylaxis of UV-induced dermatosis, in particular of polymorphic light dermatosis and its sub-forms, and/or undesired long-term consequences of UV irradiation, particularly light ageing. Preferred flavone derivatives here are, in particular, naturally occurring bioflavonoids, such as rutin, naringin, naringenin, hesperidin, hesperetin, taxifolin, etc., and derivatives thereof, such as troxerutin and monoxerutin.

European patent application EP-A-1 147 764 describes cosmetic compositions which comprise up to 10% by weight of polymethoxyflavones having at least four methoxy functions. Advantages of this composition are a skin-lightening effect in combination with prevention of wrinkles as well as storage stability and safety on use.

International patent application WO 00/61095 describes mixtures of polyphenols with vitamins. These mixtures are suitable for use in cosmetic or dermatological compositions and are optimised for scavenging free radicals, such as hydroxyl free radicals or peroxides. Particular preference is given here to the combination of troxerutin with α-tocopherol succinate and ascorbyl palmitate.

EP-A-1382329 describes compositions having light-protection properties which comprise at least one compound of the formula

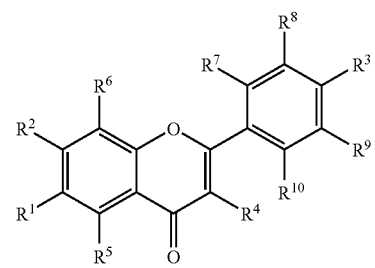

where $R^1$ and $R^2$ are selected from

H and $OR^{11}$, where each $OR^{11}$, independently of the others, is

OH, a straight-chain or branched $C_1$- to $C_{20}$-alkoxy group, a straight-chain or branched $C_3$- to $C_{20}$-alkenyloxy group, a straight-chain or branched $C_1$- to $C_{20}$-hydroxyalkoxy group, where the hydroxyl group(s) may be bonded to a primary or secondary carbon atom in the chain and furthermore the alkyl chain may also be interrupted by oxygen, and/or a $C_3$- to $C_{10}$-cycloalkoxy group and/or $C_3$- to $C_{12}$-cycloalkenyloxy group, where the rings may each also be bridged by —$(CH_2)_n$— groups, where n=1 to 3, and/or a mono- and/or oligoglycosyl radical, with the proviso that at least one radical from $R^1$ and $R^2$ is $OR^{11}$, and $R^3$ is a radical $OR^{11}$, and $R^4$ to $R^7$ and $R^{10}$ may be identical or different and are, independently of one another,

H, straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom in the chain and furthermore the alkyl chain may also be interrupted by oxygen, and/or $C_3$- to $C_{10}$-cycloalkyl groups and/or $C_3$- to $C_{12}$-cycloalkenyl groups, where the rings may each also be bridged by —$(CH_2)_n$— groups, where n=1 to 3, and $R^8$ and $R^9$ may be identical or different and are, independently of one another,

H, $OR^{11}$, straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom in the chain and furthermore the alkyl chain may also be interrupted by oxygen, and/or $C_3$- to $C_{10}$-cycloalkyl groups and/or $C_3$- to $C_{12}$-cycloalkenyl groups, where the rings may each also be bridged by —$(CH_2)_n$— groups, where n=1 to 3.

However, there continues to be a demand for skin-tolerated UV filters which are also suitable for use in skin-care compositions. In particular, there is a demand for UV filters which can easily be incorporated into aqueous phases of compositions.

The object of the invention is therefore to provide compounds or compositions which have a protective action against UV rays and/or exerts a protective action against oxidative stress on body cells and/or counters skin ageing.

Surprisingly, it has been found that certain flavonoid complexes are highly suitable as water-soluble UV filters.

The present invention therefore relates firstly to complex compounds of the formula I

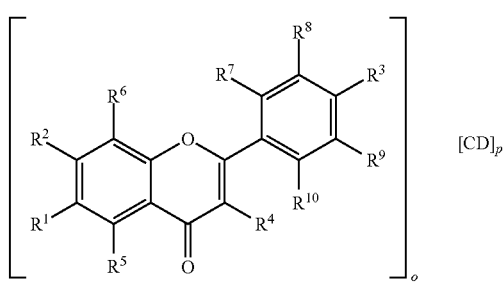

I where $R^1$ and $R^2$ are selected from

H and $OR^{11}$, where each $OR^{11}$, independently of the others, is OH, a straight-chain or branched $C_1$- to $C_{20}$-alkoxy group, a straight-chain or branched $C_3$- to $C_{20}$-alkenyloxy group, a straight-chain or branched $C_1$- to $C_{20}$-hydroxyalkoxy group, where the hydroxyl group(s) may be bonded to a primary or secondary carbon atom in the chain and furthermore the alkyl chain may also be interrupted by oxygen, and/or a $C_3$- to $C_{10}$-cycloalkoxy group and/or $C_3$- to $C_{12}$-cycloalkenyloxy group, where the rings may each also be bridged by —$(CH_2)_n$— groups, where n=1 to 3, and/or a mono- and/or oligoglycosyl radical, with the proviso that at least one radical from $R^1$ and $R^2$ stands for $OR^{11}$ and $R^4$ to $R^{10}$ may be identical or different and are, independently of one another,

H, $OR^{11}$, straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom in the chain and furthermore the alkyl chain may also be interrupted by oxygen, and/or $C_3$- to $C_{10}$-cycloalkyl groups and/or $C_3$- to $C_{12}$-cycloalkenyl groups, where the rings may each also be bridged by —$(CH_2)_n$— groups, where n=1 to 3,

| | |
|---|---|
| CD | stands for a cyclodextrin molecule |
| o | stands for the number 1 and |
| p | stands for a number from the range 0.5 to 50. |

The present application relates secondly to compositions comprising a suitable vehicle, characterised in that the compositions comprise 0.005 to 99% by weight of a complex compound of the formula I according to claim 1 or the compositions comprise 0.002 to 70% by weight of cyclodextrin and 0.001 to 60% by weight of at least one compound of the formula II or topically tolerated salts and/or derivatives thereof

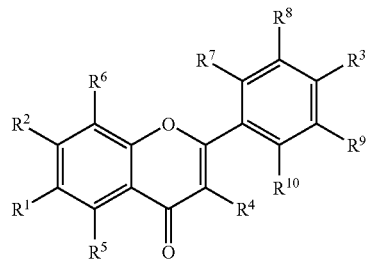

II where $R^1$ and $R^2$ are selected from

H and $OR^{11}$, where each $OR^{11}$, independently of the others, is OH, a straight-chain or branched $C_1$- to $C_{20}$-alkoxy group, a straight-chain or branched $C_3$- to $C_{20}$-alkenyloxy group, a straight-chain or branched $C_1$- to $C_{20}$-hydroxyalkoxy group, where the hydroxyl group(s) may be bonded to a primary or secondary carbon atom in the chain and furthermore the alkyl chain may also be interrupted by oxygen, and/or a $C_3$- to $C_{10}$-cycloalkoxy group and/or $C_3$- to $C_{12}$-cycloalkenyloxy group, where the rings may each also be bridged by —$(CH_2)_n$— groups, where n=1 to 3, and/or a mono- and/or oligoglycosyl radical, with the proviso that at least one radical from $R^1$ and $R^2$ stands for $OR^{11}$ and $R^3$ to $R^{10}$ may be identical or different and are, independently of one another,

H, $OR^{11}$, straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom in the chain and furthermore the alkyl chain may also be interrupted by oxygen, and/or $C_3$- to $C_{10}$-cycloalkyl groups and/or $C_3$- to $C_{12}$-cycloalkenyl groups, where the rings may each also be bridged by —$(CH_2)_n$— groups, where n=1 to 3.

Advantages of the compounds according to the invention or the compositions comprising these compounds here are, in particular, the UV-light-filtering action and the good skin tolerability. In addition, the compounds described here are colourless or have only a weak colour and thus, in contrast to many known naturally occurring flavonoids, do not result in discoloration of the compositions. Furthermore, the improved water solubility of the complexes compared with the basic compounds is advantageous in the preparation and use of formulations.

The compositions according to the invention here are usually either compositions which can be used topically, for example cosmetic or dermatological formulations, or medicaments or foods or food supplements or cosmetics to be used orally. The compositions comprise a vehicle which is suitable cosmetically or dermatologically or pharmaceutically or for foods and optionally further suitable ingredients, depending on the desired property profile.

In a preferred embodiment of the present invention, the compositions are sprayable compositions. In particular, it may be advantageous here for these compositions to be built up on an aqueous or aqueous-alcoholic vehicle basis.

Preference is given here to the use of aerosols. An aerosol is a disperse system in which a solid or liquid is extremely finely dispersed in a gas. The aerosol will itself generally only be formed on use with the aid of a suitable spray system by spraying solutions, emulsions or suspensions, to which end it is possible to use, for example, spray cans in which a liquefied compressed gas serves as propellant gas. On opening the pressure valve, the propellant/composition mixture escapes through a fine nozzle, the propellant evaporates and leaves the finely dispersed spray material behind as aerosol.

Active ingredients can be either dissolved in aerosol formulations or present in solid form; if they are in solid form, however, they must be correspondingly suspended in the propellant system.

Cosmetic and dermatological skin-care compositions based on emulsions which can be sprayed as aerosol are generally O/W systems in which hydrophilic active compounds are dissolved in the external water phase. The oil phase frequently comprises silicone-containing oils, which contribute to a pleasant skin feel after spraying.

Propellant gases which can be employed here are hydrophilic propellant gases—such as, for example, carbon dioxide—or lipophilic propellants, such as, for example, hydrocarbons. Other preferred compositions are pump sprays, in which the product is dispensed into an atomiser bottle and atomised by mechanical ejection.

Suitable sprayable W/O emulsions are, for example, those disclosed in the specifications DE-10162844-A1, DE-10162842-A1, DE-10162841-A1, DE-10162840-A1 or DE-10048683-A1.

Also suitable are W/O emulsions which can be sprayed as aerosols at room temperature, as described in WO2004030641, Emulsions of this type contain a fat phase which comprises at least 90% by weight of oil components which are liquid at room temperature and at most 4% by weight of substances selected from the group of the C3 to C4 esters of C12- to C18-alkanoic acids, C8- to C12-alkanols and silicone oils, and 20 to 85% by weight—based on the total weight of the composition—of water, and one or more W/O emulsifiers and one or more lipophilic propellant gases.

The W/O emulsifier or the W/O emulsifiers is/are particularly preferably selected from the group of PEG-30 dipolyhydroxystearate, decaglyceryl heptaoleate, polyglyceryl 3-diisostearate, PEG-8 distearate, diglycerin dipolyhydroxystearate, glycerin isostearate, sorbitan isostearate, polyglyceryl-3 methylglucose distearate, fatty alcohols having 8 to 30 carbon atoms, oligo- or polyglycerin ethers, cetyl dimethicone copolyols, alkyl methicone copolyols, alkyl dimethicone ethoxy glucoside, W/O emulsifiers which are additionally (poly 5)ethoxylated and/or (poly)propoxylated, for example polyethoxylated hydrogenated or unhydrogenated castor oil, ethoxylated cholesterol, ethoxylated fatty alcohols, such as steareth-2, ethoxylated fatty acids, such as PEG-2 stearate, PEG-40 sorbitan perisostearate. The W/O emulsifier(s) is (are) preferably selected from the group PEG-30 dipolyhydroxystearate, polyglyceryl-3 diisostearate (=polyglycerin-3 diisostearate), diglycerin dipolyhydroxystearate, glycerin isostearate, cetyl PEG/PPG-10/1 dimethicone, sorbitan isostearate, polyglyceryl-3 methylglucose distearate, steareth-2, PEG-2 stearate, sorbitan stearate, cetyl alcohol, stearyl alcohol and/or cetearyl alcohol.

Very particular preference is given to the use of combinations of the above-mentioned W/O emulsifiers, in particular a combination of two emulsifiers The W/O emulsifier used or the W/O emulsifiers used in accordance with the invention is or are advantageously present in concentrations of 0.5 to 8% by weight (based on the total weight of the composition), although it is possible and advantageous to keep the content of emulsifiers low, for example up to 5% by weight, in each case based on the total weight of the composition. It may furthermore be advantageous to select the emulsifiers in such a way that combinations of W/O and O/W emulsifiers are used.

It may be advantageous for the compositions additionally to comprise stabilisers. The stabiliser used is preferably PEG-45/dodecyl glycol copolymer and/or PEG 22/dodecyl glycol copolymer and/or methoxy PEG-22/dodecyl glycol copolymer 10. Furthermore, poloxamers of the Pluronic type may also be preferred. The stabiliser(s) are advantageously present in concentrations of O to 8% by weight, although it is possible and advantageous to keep the content of stabilisers low, for example up to 5% by weight, in each case based on the total weight of the composition. It is very particularly advantageous to use stabilisers if the pH of the compositions is in the acidic range. It is very particularly preferred for combinations of the above-mentioned W/O emulsifiers and a stabiliser to be employed.

If the compositions according to the invention comprise UV filter substances, it is advantageous for the oil phase to comprise butylene glycol derivatives (such as, for example, butylene glycol dicaprylate), triglycerides (such as, for example, caprylic/capric triglcyeride, C2-C5 alkyl benzoate and/or silicone oils or to consist entirely of such oils.

The amount of water can be up to about 85% by weight, based on the total weight of the compositions, where optimum water contents are usually selected in the range between 50 and 80% by weight.

The sprayable compositions according to the invention exhibit very good sensory properties, such as, for example, spreadability on the skin or ability to be absorbed into the skin, and are, in addition, distinguished by above-average skin care and a pleasant cooling effect.

Cyclodextrins are built up from 6, 7, 8 or even more α-1,4-linked glucose units, with cyclohexaamylose (alpha- or α-cyclodextrin) being distinguished by the structure

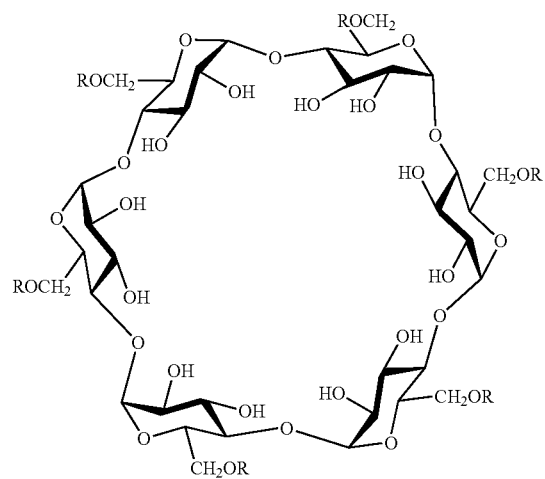

Cycloheptaamylose (beta- or β where bonded to this glycoside radical, in each case via an —O— group, is at least one radical selected from β-cyclodextrin) is distinguished by the structure

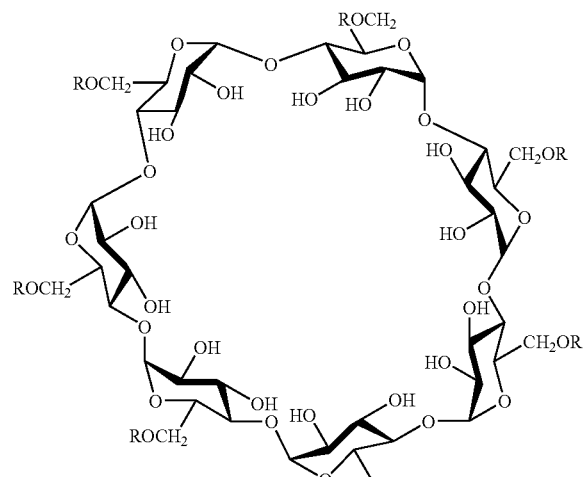

Cyclooctaamylose (gamma- or γ-cyclodextrin) is distinguished by the structure

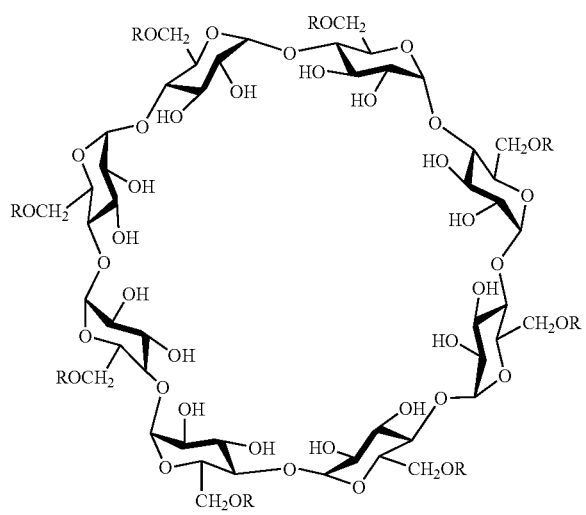

Cycloenneaamylose (delta- or δ-cyclodextrin) is distinguished by the structure

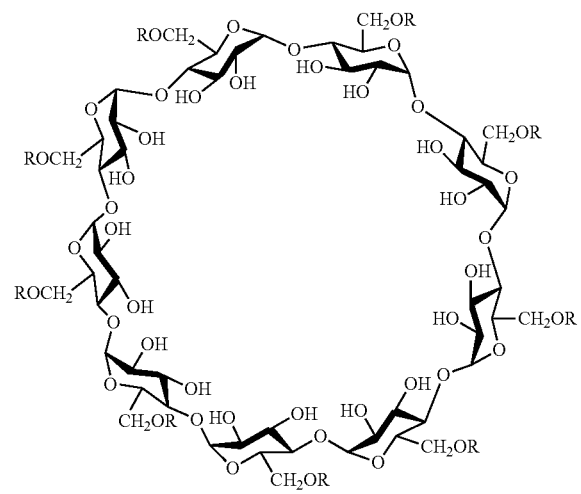

Cyclodextrins may occur in underivatised form (R═H) or also in derivatised form, for example alkoxylated, hydroxyalkylated or alkylated, in particular propoxylated or methylated, in position R.

Bioflavonoid/cyclodextrin complexes are known in principle:

K. Miyake, H. Arima et al. (Pharm. Dev. Techn. 5(3) 2000, 399-407 describe 1:1 complexes of rutin with beta-cyclodextrins and the solubility and liberation behaviour thereof. It was found here that the beta-cyclodextrin complex and the 2-hydroxypropyl-beta-cyclodextrin complex are particularly stable. Alpha- and gamma-cyclodextrin complexes are, according to this publication, generally less suitable for complexing rutin than are beta-cyclodextrin complexes.

T. K. Nguyen, H. Galons, C. Chemtob, Congr. Int. Technol. Pharm., 6th (1992), Vol 5, 408-16408-416 likewise describe various cyclodextrin complexes of rutin. The 2,6-di-O-methyl-beta-cyclodextrin complex proves to be particularly soluble here, with complexes having rutin:cyclodextrin molar ratios of 1:1 and 1:2 being described.

Complexes of isoflavones in soya beans or fermented soya beans with beta- and gamma-cyclodextrins are described in European Patent Application EP-A-796 624. The complexing increases the solubility of isoflavones and reduces their bitterness.

Rutin complexes with beta- and gamma-cyclodextrins and the use thereof as antioxidant are described in Japanese Patent Application JP 05/9137499.

Beverages comprising cyclodextrin complexes of quercetin glycosides are described in Japanese Patent Application JP 07/075536.

Japanese Patent Application JP 05/186344 describes compositions comprising vitamin C and cyclodextrin complexes of vitamin P which improve the bioabsorption of vitamin C. Complexes of rutin, hesperidin and eriocitrin, such as, for example, a rutin/beta-cyclodextrin complex having a molar ratio of 1.2, are described.

The action of a complex of 3-methoxyquercetin with hydroxypropyl-beta-cyclodextrin on nasal epithelial cells is investigated in S. Dimova, R. Mugabowindekwe et al. Int. J. Pharm. 26381-2) 2003, 95-103.

Beta-cyclodextrin complexes of various flavonoids (hesperetin, hesperidin, naringenin, naringin) are characterised in R. Ficarra, S. Tommasini et al.; J. Pharm. Biomed. Analysis 29(6) 2002, 1005-1014.

R.-L. Wang, Yu Yang et al.; Yingyong Huaxue 19(7) 2002 702-704 compare the stability and solubility of various beta-cyclodextrin complexes of various flavonoids (rutin, quercetin, morin). Methyl-beta-cyclodextrin complexes proved to have particularly high solubility here.

K. Hostettmann, M. Lederer and A. Marston; Phytochemical Analysis 1186) 2000, 380-382 investigate the eluting action of 2-hydroxypropyl-beta-cyclodextrin on flavonoids absorbed on cellulose.

It has been found, in an unforeseeable manner for the person skilled in the art, that compositions for topical use comprising the above-mentioned complex compounds of the formula I or compounds of the formula II and cyclodextrins remedy the disadvantages of the prior art.

It is particularly advantageous here if the cyclodextrins used are cyclodextrins which are substituted by $C_{1-24}$-alkyl or $C_{1-24}$-hydroxyalkyl on one or more hydroxyl groups, such as, in particular, hydroxypropylcyclodextrin, or mixtures of cyclodextrins which comprise at least 30% by weight, based on the total weight of the cyclodextrin mixture, of the above-mentioned cyclodextrins. Particular preference is given here to the use of β- or γ-cyclodextrins.

It is furthermore advantageous for the content of cyclodextrins to be 0.01-20.0% by weight, preferably 0.05-10.0% by weight, particularly preferably 0.1-5.0% by weight, in each case based on the total weight of the composition. The proportion of the compounds of the formula II in the composition here is preferably 0.01 to 20% by weight, particularly preferably 0.05 to 10% by weight and especially preferably 0.1 to 5% by weight, based on the composition as a whole. The proportion of the compounds of the formula II in the composition is very particularly preferably 0.1 to 2% by weight, based on the composition as a whole.

Advantageous in accordance with the invention is the use of cyclodextrins and/or cyclodextrin derivatives for increasing the solubility of compounds of the formula II. Furthermore advantageous is the use of cyclodextrins and/or cyclodextrin derivatives for improving the biological efficacy of compounds of the formula II.

The active-ingredient combinations in accordance with the invention or cosmetic or dermatological compositions comprising such active-ingredient combinations are satisfactory preparations in every respect. It was not foreseeable for the person skilled in the art that the compositions in accordance with the invention provide compounds of the formula II in increased availability, protect the skin against environmental influences better than the compositions of the prior art.

The present invention therefore furthermore also relates to the use of the compounds of the formula I, as indicated above, as UV filters or for the preparation of a composition having light-protection properties.

The compositions here are usually compositions which can be applied topically, for example cosmetic or dermatological formulations. The compositions in this case comprise a cosmetically or dermatologically suitable vehicle and, depending on the desired property profile, optionally further suitable ingredients.

The flavonoids of the formula I to be employed in accordance with the invention include broad-band UV filters, which can be employed alone or in combination with further UV filters.

Other, likewise preferred compounds of the formula I exhibit an absorption maximum in the boundary region between UV-B and UV-A radiation. As UV-A II filters, they therefore advantageously supplement the absorption spectrum of commercially available UV-B and UV-A I filters.

Preferred compositions according to the invention having light-protection properties comprise at least one compound of the formula I, where $R^3$ stands for OH or straight-chain or branched $C_1$- to $C_{20}$-alkoxy groups, preferably methoxy, ethoxy or ethylhexyloxy, or mono- and/or oligoglycosyl radicals, preferably glucosyl radicals, and $R^1$ and/or $R^2$ preferably stand for OH or straight-chain or branched $C_1$- to $C_{20}$-alkoxy groups, preferably methoxy, ethoxy or ethylhexyloxy, or mono- and/or oligoglycosyl radicals, preferably glucosyl radicals.

These preferred compounds are distinguished by particularly intensive UV absorption.

Preferred mono- or oligosaccharide radicals here are hexosyl radicals, in particular ramnosyl radicals and glucosyl radicals. However, other hexosyl radicals, for example allosyl, altrosyl, galactosyl, gulosyl, idosyl, mannosyl and talosyl, can optionally advantageously also be used. It may also be advantageous to use pentosyl radicals. The glycosyl radicals may be α- or β-glycosidically linked to the parent structure. A preferred disaccharide is, for example, 6-O-(6-deoxy-α-L-mannopyranosyl)-β-D-glucopyranoside.

In likewise preferred embodiments of the invention, however, the compositions according to the invention may also comprise compounds of the formula I which are sparingly soluble or insoluble in the composition matrix. In this case, the compounds are preferably dispersed in finely divided form in the cosmetic composition.

According to knowledge to date, the radicals $R^4$ to $R^7$ and $R^{10}$ only have an insignificant effect on the desired molar UV absorption and, for the purposes of the present invention, are therefore regarded as substantially inert with respect to UV absorption. It may therefore be preferred in accordance with the invention for $R^4$ to $R^7$ and $R^{10}$ to be identical or different and to stand, independently of one another, for

H straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom in the chain and furthermore the alkyl chain may also be interrupted by oxygen, and/or $C_3$- to $C_{10}$-cycloalkyl groups and/or $C_3$- to $C_{12}$-cycloalkenyl groups, where the rings may in each case also be bridged by —$(CH_2)_n$— groups, where n=1 to 3.

However, since the absorption per gram of substance for the composition is significant, particular preference is given in accordance with the invention to compounds of the formula I or compositions which comprise at least one compound of the formula I which is characterised in that $R^4$ to $R^7$ and $R^{10}$ are H.

It has been found that the intensity of UV absorption is particularly high if $R^3$ stands for straight-chain or branched $C_1$- to $C_{20}$-alkoxy groups, preferably methoxy, ethoxy or ethylhexyloxy, and $R^8$ and $R^9$ are identical and stand for H or straight-chain or branched $C_1$- to $C_{20}$-alkoxy groups, preferably methoxy, ethoxy or ethylhexyloxy.

Particular preference is therefore given in accordance with the invention to compositions having light-protection properties comprising at least one compound of the formula I which is characterised in that $R^3$ stands for straight-chain or branched $C_1$- to $C_{20}$-alkoxy groups, preferably methoxy, ethoxy or ethylhexyloxy, and $R^8$ and $R^9$ are identical and stand for H or straight-chain or branched $C_1$- to $C_{20}$-alkoxy groups, preferably methoxy, ethoxy or ethylhexyloxy. It is particularly preferred here for $R^8$ and $R^9$ to stand for H.

In accordance with the invention, the compounds of the formula I are typically employed in amounts of 0.01 to 20% by weight, preferably in amounts of 0.5% by weight to 10% by weight and particularly preferably in amounts of 1 to 8% by weight. The person skilled in the art is presented with absolutely no difficulties here in selecting the amounts appropriately depending on the intended light-protection factor of the composition.

Compositions which are particularly preferred in accordance with the invention comprise, as stated above, further UV filters, preferably UV-B and UV-A I filters, in addition to the compounds of the formula I.

On use of the dibenzoylmethane derivatives which are particularly preferred as UV-A filters in combination with the compounds of the formula I, an additional advantage arises: the UV-sensitive dibenzoylmethane derivatives are additionally stabilised by the presence of the compounds of the formula I. The present invention therefore furthermore relates to the use of the compounds of the formula I for the stabilisation of dibenzoylmethane derivatives in compositions.

In principle, all UV filters are suitable for combination with the compounds of the formula I according to the invention. Particular preference is given to UV filters whose physiological acceptability has already been demonstrated. Both for UVA and UVB filters, there are many proven substances known from the specialist literature, for example benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl]-benzyl}acrylamide (for example Mexoryl® SW), N,N,N-trimethyl-4-(2-oxoborn-3-ylidenemethyl)anilinium methylsulfate (for example Mexoryl® SK) or (2-oxoborn-3-ylidene)toluene-4-sulfonic acid (for example Mexoryl® SL), benzoyl- or dibenzoylmethanes, such as 1-(4-tert-butylphenyl)-3-(4-methoxyphenyl)propane-1,3-dione (for example Eusolex® 9020) or 4-isopropyldibenzoylmethane (for example Eusolex® 8020), benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40), methoxycinnamic acid esters, such as octyl methoxycinnamate (for example Eusolex® 2292), isopentyl 4-methoxycinnamate, for example as a mixture of the isomers (for example Neo Heliopan® E 1000), salicylate derivatives, such as 2-ethylhexyl salicylate (for example Eusolex® OS), 4-isopropylbenzyl salicylate (for example Megasol®) or 3,3,5-trimethylcyclohexyl salicylate (for example Eusolex® HMS), 4-aminobenzoic acid and derivatives, such as 4-aminobenzoic acid, 2-ethylhexyl 4-(dimethylamino)benzoate (for example Eusolex® 6007), ethoxylated ethyl 4-aminobenzoate (for example Uvinul® P25), phenylbenzimidazolesulfonic acids, such as 2-phenylbenzimidazole-5-sulfonic acid and potassium, sodium and triethanolamine salts thereof (for example Eusolex® 232), 2,2-(1,4-phenylene)bisbenzimidazole-4,6-disulfonic acid and salts thereof (for example Neoheliopan® AP) or 2,2-(1,4-phenylene)bisbenzimidazole-6-sulfonic acid;

and further substances, such as 2-ethylhexyl 2-cyano-3,3-diphenylacrylate (for example Eusolex® OCR), 3,3'-(1,4-phenylenedimethylene)bis(7,7-dimethyl-2-oxobicyclo[2.2.1]hept-1-ylmethanesulfonic acid and salts thereof (for example Mexoryl® SX) and 2,4,6-trianilino-(p-carbo-2'-ethylhexyl-1'-oxy)-1,3,5-triazine (for example Uvinul® T 150)

hexyl 2-(4-diethylamino-2-hydroxybenzoyl)benzoate (for example Uvinul® UVA Plus, BASF).

The compounds mentioned in the list should only be regarded as examples. It is of course also possible to use other UV filters.

These organic UV filters are generally incorporated into cosmetic formulations in an amount of 0.5 to 10 percent by weight, preferably 1-8%.

Further suitable organic UV filters are, for example, 2-(2H-benzotriazol-2-yl)-4-methyl-6-(2-methyl-3-(1,3,3,3-tetramethyl-1-(trimethylsilyloxy)disiloxanyl)propyl)phenol (for example Silatrizole®), 2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB), α-(trimethylsilyl)-ω-[trimethylsilyl)oxy]poly[oxy[dimethyl [and approximately 6% of methyl[2-[p-[2,2-bis(ethoxycarbonyl)vinyl]phenoxy]-1-methyleneethyl] and approximately 1.5% of methyl[3-[p-[2,2-bis(ethoxycarbonyl)vinyl])phenoxy)propenyl) and 0.1 to 0.4% of (methylhydrogen)silylene]] (n≈60) (CAS No. 207 574-74-1)

2,2'-methylenebis(6-(2H-benzotriazol-2-yl)-4-(1,1,3,3-tetramethylbutyl)phenol) (CAS No. 103 597-45-1)

2,2'-(1,4-phenylene)bis(1H-benzimidazole-4,6-disulfonic acid, monosodium salt) (CAS No. 180 898-37-7) and 2,4-bis{[4-(2-ethylhexyloxy)-2-hydroxy]phenyl}-6-(4-methoxyphenyl)-1,3,5-triazine (CAS No. 103 597-45-, 187 393-00-6).

2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB), Organic UV filters are generally incorporated into cosmetic formulations in an amount of 0.5 to 20 percent by weight, preferably 1-15%.

Conceivable inorganic UV filters are those from the group of the titanium dioxides, such as, for example, coated titanium dioxide (for example Eusolex® T-2000, Eusolex® T-AQUA), zinc oxides (for example Sachtotec®), iron oxides or also cerium oxides. These inorganic UV filters are generally incorporated into cosmetic compositions in an amount of 0.5 to 20 percent by weight, preferably 2-10%.

Preferred compounds having UV-filtering properties are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and the potassium, sodium and triethanolamine salts thereof.

Combination of one or more compounds of the formula I with further UV filters enables the protective action against damaging effects of UV radiation to be optimised.

Optimised compositions may comprise, for example, the combination of the organic UV filters 4'-methoxy-6-hydroxy-flavone/CD with 1-(4-tert-butylphenyl)-3-(4-methoxyphenyl)propane-1,3-dione and 3-(4'-methylbenzylidene)-dl-camphor. This combination gives rise to broad-band protection, which can be supplemented by the addition of inorganic UV filters, such as titanium dioxide microparticles.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables composition problems caused by the interaction of individual composition constituents with one another, such as crystallisation processes, precipitation and agglomerate formation, to be avoided since the interaction is suppressed.

It is therefore preferred in accordance with the invention for one or more of the above-mentioned UV filters to be in encapsulated form. It is advantageous here for the capsules to be so small that they cannot be viewed with the naked eye. In order to achieve the above-mentioned effects, it is furthermore necessary for the capsules to be sufficiently stable and the encapsulated active ingredient (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules which can particularly preferably be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules are preferably present in compositions according to the invention in amounts which ensure that the encapsulated UV filters are present in the composition in the above-indicated amounts.

If the compounds according to the invention have free hydroxyl groups, they additionally, besides the properties described, exhibit an action as antioxidant and/or free-radical scavenger. Preference is therefore also given to compositions having light-protection properties comprising at least one compound of the formula I which is characterised in that at least one of the radicals $R^1$ to $R^3$ stands for OH, where at least one of the radicals $R^1$ and $R^2$ preferably stands for OH.

In order that the compounds of the formula I are able to develop their positive action as free-radical scavengers on the skin particularly well, it may be preferred to allow the compounds of the formula I to penetrate into deeper skin layers. Several possibilities are available for this purpose. Firstly, the compounds of the formula I can have an adequate lipophilicity in order to be able to penetrate through the outer skin layer into epidermal layers. As a further possibility, corresponding transport agents, for example liposomes, which enable transport of the compounds of the formula I through the outer skin layers may also be provided in the composition. Finally, systemic transport of the compounds of the formula I is also conceivable. The composition is then designed, for example, in such a way that it is suitable for oral administration.

In general, the substances of the formula I act as free-radical scavengers. Free radicals of this type are not generated only by sunlight, but instead are formed under various conditions. Examples are anoxia, which blocks the flow of electrons upstream of the cytochrome oxidases and causes the formation of superoxide free-radical anions; inflammation associated, inter alia, with the formation of superoxide anions by the membrane NADPH oxidase of the leucocytes, but also associated with the formation (through disproportionation in the presence of iron(II) ions) of the hydroxyl free radicals and other reactive species which are normally involved in the phenomenon of phagocytosis; and lipid autoxidation, which is generally initiated by a hydroxyl free radical and produces lipidic alkoxy free radicals and hydroperoxides.

It is assumed that the preferred compounds of the formula I also act as enzyme inhibitors. They presumably inhibit histidine decarboxylase, protein kinases, elastase, aldose reductase and hyaluronidase, and therefore enable the intactness of the basic substance of vascular sheaths to be maintained. Furthermore, they presumably inhibit non-specifically catechol O-methyl transferase, causing the amount of available catecholamines and thus the vascular strength to be increased. Furthermore, they inhibit AMP phosphodiesterase, giving the substances potential for inhibiting thrombocyte aggregation.

Owing to these properties, the compositions according to the invention are, in general, suitable for immune protection and for the protection of DNA and RNA. In particular, the compositions are suitable for the protection of DNA and RNA against oxidative attack, against free radicals and against damage due to radiation, in particular UV radiation. A further advantage of the compositions according to the invention is cell protection, in particular protection of Langerhans cells against damage due to the above-mentioned influences. All these uses and the use of the compounds of the formula I for the preparation of compositions which can be employed correspondingly are expressly also a subject-matter of the present invention.

In particular, preferred compositions according to the invention are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leukoplakia, leukoplakiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammation which is not associated with a defect in keratinisation, for the treatment of all benign or malignant excrescence of the dermis or epidermis, which may be of viral origin, such as verruca vulgaris. verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in sebum production, such as hyperseborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, for the treatment of skin problems caused by UV radiation.

The protective action against oxidative stress or against the effect of free radicals can be further improved if the compositions comprise one or more further antioxidants.

In a preferred embodiment of the present invention, the composition is therefore a composition for the protection of body cells against oxidative stress, in particular for reducing skin ageing, characterised in that it preferably comprises one or more antioxidants.

There are many proven substances known from the specialist literature which can be used as antioxidants, for example amino acids (for example glycine, histidine, tyrosine, tryptophan) and derivatives thereof, imidazoles, (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to µmol/kg), and also (metal) chelating agents, (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acid and derivatives thereof, mannose and derivatives thereof, zinc and derivatives therof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the cosmetic compositions according to the invention. Known and commercial mixtures are, for example, mixtures comprising, as active ingredients, lecithin, (L-(+)- ascorbyl palmitate and citric acid (for example (for example Oxynex ® AP), natural tocopherols, L-(+)-ascorbyl palmitate, L-(+)-ascorbyl acid and citric acid (for example Oxynex ® K LIQUID), tocopherol extracts from natural sources, L-(+)-ascorbyl palmitate, L-(+)-ascorbic acid and citric acid (for example Oxynex ® L LIQUID), DL-α-tocopherol, L-(+)-ascorbyl palmitate, citric acid and lecithin (for example Oxynex ® LM) or butylhydroxytoluene (BHT), L-(+)-ascorbyl palmitate and citric acid (or example Oxynes ® 2004). Antioxidants of this type are usually employed with compounds of the formula I in such compositions in ratios in the range from 1000:1 to 1:1000, preferably in amounts of 100:1 to 1:100.

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin D phd 2), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine, (vitamin $B_6$), pantothenic acid, biotin, folic acid and cobalamine anisole, nordihydroguaiaretic acid, trihydroxybutyrophenone, quercetin, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid (for example (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed with compounds of the formula I in such compositions in ratios in the range from 1000:1 to 1:1000, preferably in amounts of 100:1 to 1:100.

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin B$_1$), riboflavin (vitamin B$_2$), nicotinamide, vitamin C (ascorbic acid), vitamin D, ergocalciferol (vitamin D$_2$), vitamin E, DL-α-tocopherol, tocopherol E acetate, tocopherol hydrogensuccinate, vitamin K$_1$, esculin (vitamin P active ingredient), thiamine (vitamin B$_1$), nicotinic acid (niacin), pyridoxine, pyridoxal, pyridoxamine, (vitamin B$_6$), pantothenic acid, biotin, folic acid and cobalamine acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxy-(vitamin B$_{12}$), particularly preferably vitamin A palmitate, vitamin C, DL-α-tocopherol, tocopherol E acetate, nicotinic acid, pantothenic acid and biotin. Vitamins are usually employed here with compounds of the formula I in ratios in the range from 1000:1 to 1:1000, preferably in amounts of 100:1 to 1:100.

The compositions according to the invention may in addition comprise further conventional skin-protecting or skin-care active ingredients. These may in principle be any active ingredients known to the person skilled in the art.

These may be chromone derivatives. The term chromone derivatives here is preferably taken to mean certain chromen-2-one derivatives which are suitable as active ingredients for the preventive treatment of human skin and human hair against ageing processes and harmful environmental influences. At the same time, they exhibit a low irritation potential for the skin, have a positive effect on water binding in the skin, maintain or increase the elasticity of the skin and thus promote smoothing of the skin. These compounds preferably conform to the formula IV

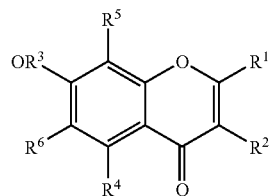

where
R$^1$ and R$^2$ may be identical or different and are selected from
  H, —C(=O)—R$^7$, —C(=O)—OR$^7$,
  straight-chain or branched C$_1$- to C$_{20}$-alkyl groups,
  straight-chain or branched C$_3$- to C$_{20}$-alkenyl groups,
  straight-chain or branched C$_1$- to C$_{20}$-hydroxyalkyl groups, where the hydroxyl group may be bonded to a primary or secondary carbon atom in the chain and furthermore the alkyl chain may also be interrupted by oxygen, and/or
  C$_3$- to C$_{10}$-cycloalkyl groups and/or C$_3$- to C$_{12}$-cycloalkenyl groups, where the rings may each also be bridged by —(CH$_2$)$_n$— groups, where n=1 to 3,
R$^3$ stands for H or straight-chain or branched C$_1$- to C$_{20}$-alkyl groups,
R$^4$ stands for H or OR$^8$,
R$^5$ and R$^6$ may be identical or different and are selected from
  —H, —OH,
  straight-chain or branched C$_1$- to C$_{20}$-alkyl groups,
  straight-chain or branched C$_3$- to C$_{20}$-alkenyl groups,
  straight-chain or branched C$_1$- to C$_{20}$-hydroxyalkyl groups, where the hydroxyl group may be bonded to a primary or secondary carbon atom in the chain and furthermore the alkyl chain may also be interrupted by oxygen, and
R$^7$ stands for H, straight-chain or branched C$_1$- to C$_{20}$-alkyl groups, a polyhydroxyl compound, such as preferably an ascorbic acid radical or glycosidic radicals, and
R$^8$ stands for H or straight-chain or branched C$_1$- to C$_{20}$-alkyl groups, where at least 2 of the substituents R$^1$, R$^2$, R$^4$-R$^6$ are not H or at least one substituent from R$^1$ and R$^2$ stands for —C(=O)—R$^7$ or —C(=O)—OR$^7$.

The proportion of one or more compounds selected chromone derivatives in the composition according to the invention is preferably from 0.001 to 5% by weight, particularly preferably from 0.01 to 2% by weight, based on the composition as a whole.

It may furthermore be preferred for the composition according to the invention to comprise at least one repellent, where the repellent is preferably selected from N,N-diethyl-3-methylbenzamide, ethyl 3-(acetylbutylamino)propionate, dimethyl phthalate, butopyronoxyl, 2,3,4,5-bis(2-butylene) tetrahydro-2-furaldehyde, N,N-diethylcaprylamide, N,N-diethylbenzamide, o-chloro-N,N-diethylbenzamide, dimethyl carbate, di-n-propyl isocinchomeronate, 2-ethylhexane-1,3-diol, N-octylbicycloheptenedicarboximide, piperonyl butoxide, 1-(2-methylpropoxycarbonyl)-2-(hydroxyethyl)piperidine, or mixtures thereof, where it is particularly preferably selected from N,N-diethyl-3-methylbenzamide, ethyl 3-(acetylbutylamino)propionate 1-(2-methylpropoxycarbonyl)-2-(hydroxyethyl)piperidine, or mixtures thereof.

The compositions according to the invention which comprise repellents are preferably insect repellents. Insect repellents are available in the form of solutions, gels, sticks, rollers, pump sprays and aerosol sprays, with solutions and sprays forming the majority of the commercially available products.

The basis for these two product forms is usually formed by alcoholic or aqueous/alcoholic solutions with addition of fatting substances and slight perfuming.

Particularly preferred active ingredients are pyrimidinecarboxylic acids and/or aryl oximes.

Pyrimidinecarboxylic acids occur in halophilic microorganisms and play a role in osmoregulation of these organisms (E. A. Galinski et al., *Eur. J. Biochem.*, 149 (1985) page 135-139). Of the pyrimidinecarboxylic acids, particular mention should be made here of ectoin ((S)-1,4,5,6-tetrahydro-2-methyl-4-pyrimidinecarboxylic acid) and hydroxyectoin ((S, S)-1,4,5,6-tetrahydro-5-hydroxy-2-methyl-4-pyrimidinecarboxylic acid and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoin and ectoin derivatives, such as hydroxyectoin, can advantageously be used in medicaments. In particular, hydroxyectoin can be employed for the preparation of a medicament for the treatment of skin diseases. Other areas of application of hydroxyectoin and other ectoin derivatives are typically in areas in which, for example, trehalose is used as additive. Thus, ectoin derivatives, such as hydroxyectoin, can be used as protectant in dried yeast and bacterial cells. Pharmaceutical products, such as non-glycosylated, pharmaceutical active peptides and proteins, for example t-PA, can also be protected with ectoin or its derivatives.

Of the cosmetic applications, particular mention should be made of the use of ectoin and ectoin derivatives for the care of aged, dry or irritated skin. Thus, European patent application EP-A-0 671 161 describes, in particular, that ectoin and hydroxyectoin are employed in cosmetic compositions, such as powders, soaps, surfactant-containing cleansing products, lipsticks, rouge, make-ups, care creams and sunscreen preparations.

Preference is given here to the use of a pyrimidinecarboxylic acid of the following formula V

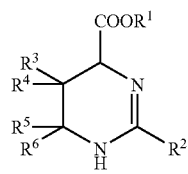

V in which $R^1$ is a radical H or C1-8-alkyl, $R^2$ is a radical H or C1-4-alkyl and $R^3$, $R^4$, $R^5$ and $R^6$ are each, independently of one another, a radical from the group H, OH, $NH_2$ and C1-4-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoin ((S)-1,4,5,6-tetrahydro-2-methyl-4-pyrimidinecarboxylic acid) and hydroxyectoin ((S, S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight. The pyrimidinecarboxylic acids are preferably employed here in ratios of 100:1 to 1:100 with respect to the compounds of the formula I, with ratios in the range 1:10 to 10:1 being particularly preferred.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and skin appendages. Compositions according to the invention which, in addition to the compound of the formula I, additionally comprise an aryl oxime, preferably 2-hydroxy-5-methyllaurophenone oxime, exhibit surprising antiinflammatory suitability. The compositions here preferably comprise 0.01 to 10% by weight of the aryl oxime, it being particularly preferred for the composition to comprise 0.05 to 5% by weight of aryl oxime.

In a further, likewise preferred embodiment of the present invention, the composition according to the invention comprises at least one self-tanning agent.

Advantageous self-tanning agents which can be employed are, inter alia:

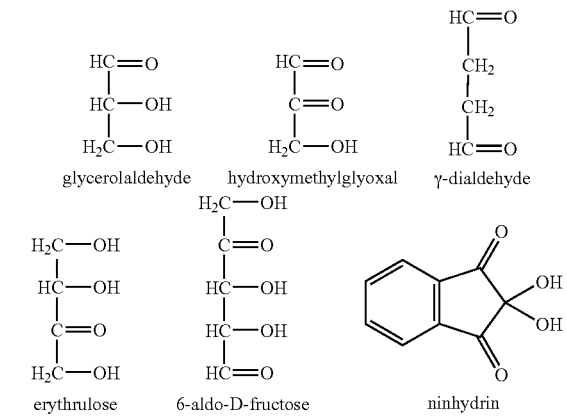

Mention should also be made of 5-hydroxy-1,4-naphthoquinone (juglone), which is extracted from the shells of fresh walnuts

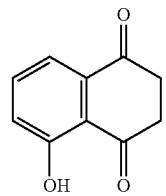

5-hydroxy-1,4-naphthoquinone (juglone)
and 2-hydroxy-1,4-naphthoquinone (lawsone), which occurs in henna leaves.

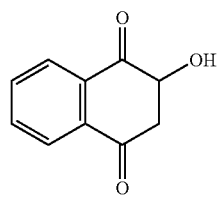

2-hydroxy-1,4-naphthoquinone (lawsone)

Very particular preference is given to 1,3-dihydroxyacetone (DHA), a trifunctional sugar which occurs in the human body, and derivatives thereof.

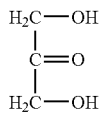

1,3-dihydroxyacetone (DHA)

Furthermore, the compositions according to the invention may also comprise dyes and coloured pigments. The dyes and coloured pigments can be selected from the corresponding positive list in the German Cosmetics Regulation or the EC list of cosmetic colorants. In most cases, they are identical with the dyes approved for foods. Advantageous coloured pigments are, for example, titanium dioxide, mica, iron oxides (for example $Fe_2O_3$, $Fe_3O_4$, $FeO(OH)$) and/or tin oxide. Advantageous dyes are, for example, carmine, Berlin Blue, Chromium Oxide Green, Ultramarine Blue and/or Manganese Violet. It is particularly advantageous to select the dyes and/or coloured pigments from the following list. The Colour Index numbers (CINs) are taken from the Rowe Colour Index, 3rd Edition, Society of Dyers and Colourists, Bradford, England, 1971.

| Chemical or other name | CIN | Colour |
|---|---|---|
| Pigment Green | 10006 | green |
| Acid Green 1 | 10020 | Green |
| 2,4-Dinitrohydroxynaphthalene-7-sulfonic acid | 10316 | Yellow |
| Pigment Yellow 1 | 11680 | Yellow |
| Pigment Yellow 3 | 11710 | Yellow |
| Pigment Orange 1 | 11725 | Orange |
| 2,4-Dihydroxyazobenzene | 11920 | Orange |
| Solvent Red 3 | 12010 | Red |
| 1-(2'-Chloro-4'-nitro-1'-phenylazo)-2-hydroxynaphthalene | 12085 | Red |
| Pigment Red 3 | 12120 | Red |
| Ceres Red; Sudan Red; Fat Red G | 12150 | Red |
| Pigment Red 112 | 12370 | Red |
| Pigment Red 7 | 12420 | Red |
| Pigment Brown 1 | 12480 | Brown |
| 4-(2'-Methoxy-5'sulfonyldiethylamide-1'-phenylazo)-3-hydroxy-5''-chloro-2'',4''-dimethoxy2-naphthanilide | 12490 | Red |
| Disperse Yellow 16 | 12700 | Yellow |
| 1-(4-Sulfo-1-phenylazo)-4-aminobenzene-5-sulfonic acid | 13015 | Yellow |
| 2,4-Dihydroxyazobenzene-4'-sulfonic acid | 14270 | Orange |
| 2-(2,4-Dimethylphenylazo-5-sulfonyl)-1-hydroxynaphthalene-4-sulfonic acid | 14700 | Red |
| 2-(4-Sulfo-1-naphthylazo)-1-naphthol-4-sulfonic acid | 14720 | Red |
| 2-(6-Sulfo-2,4-xylylazo)-1-naphthol-5-sulfonic acid | 14815 | Red |
| 1-(4'-Sulfophenylazo)-2-hydroxynaphthalene | 15510 | Orange |
| 1-(2-Sulfonyl-4-chloro-5-carboxy-1-phenylazo)-2-hydroxynaphthalene | 15525 | Red |
| 1-(3-Methylphenylazo-4-sulfonyl)-2-hydroxynaphthalene | 15580 | Red |
| 1-(4',(8')-Sulfonylnaphthylazo)-2-hydroxynaphthalene | 15620 | Red |
| 2-Hydroxy-1,2'-azonaphthalene-1'-sulfonic acid | 15630 | Red |
| 3-Hydroxy-4-phenylazo-2-naphthylcarboxylic acid | 15800 | Red |
| 1-(2-Sulfo-4-methyl-1-phenylazo)-2-naphthylcarboxylic acid | 15850 | Red |
| 1-(2-Sulfo-4-methyl-5-chloro-1-phenylazo)-2-hydroxynaphthalene-3-carboxylic acid | 15865 | Red |

-continued

| Chemical or other name | CIN | Colour |
|---|---|---|
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | Orange |
| 1-(4-Sulfo-1-phenylazo)-2-naphthol-6-sulfonic acid | 15985 | Yellow |
| Allura Red | 16035 | Red |
| 1-(4-Sulfo-1-naphthylazo)-2-naphthol-3,6-disulfonic acid | 16185 | Red |
| Acid Orange 10 | 16230 | Orange |
| 1-(4-Sulfo-1-naphthylazo)-2-naphthol-6,8-disulfonic acid | 16255 | Red |
| 1-(4-Sulfo-1-naphthylazo)-2-naphthol-3,6,8-trisulfonic acid | 16290 | Red |
| 8-Amino-2-phenylazo-1-naphthal-3,6-disulfonic acid | 17200 | Red |
| Acid Red 1 | 18050 | Red |
| Acid Red 155 | 18130 | Red |
| Acid Yellow 121 | 18690 | Yellow |
| Acid Red 180 | 18736 | Red |
| Acid Yellow 11 | 18820 | Yellow |
| Acid Yellow 17 | 18965 | Yellow |
| 4-(4-Sulfo-1-phenylazo)-1-(4-sulfophenyl)-5-hydroxy-pyrazolone-3-carboxylic acid | 19140 | Yellow |
| Pigment Yellow 16 | 20040 | Yellow |
| 2,6-(4'-Sulfo-2'',4''-dimethyl)bisphenylazo)1,3-dihydroxy-benzene | 20170 | Orange |
| Acid Black 1 | 20470 | Black |
| Pigment Yellow 13 | 21100 | Yellow |
| Pigment Yellow 83 | 21108 | Yellow |
| Solvent Yellow | 21230 | Yellow |
| Acid Red 163 | 24790 | Red |
| Acid Red 73 | 27290 | Red |
| 2-[4'-(4''-Sulfo-1''-phenylazo)-7'-sulfo-1'-naphthylazo]-1-hydroxy-7-aminonaphthalene-3,6-disulfonic acid | 27755 | black |
| 4-[4''-Sulfo-1''-phenylazo)-7'-sulfo-1'-naphthylazo]-1-hydroxy-8-acetylaminonaphthalene-3,5-disulfonic acid | 28440 | Black |
| Direct Orange 34, 39, 44, 46, 60 | 40215 | Orange |
| Food Yellow | 40800 | Orange |
| trans-β-Apo-8'-carotene aldehyde ($C_{30}$) | 40820 | Orange |
| trans-Apo-8'-carotinic acid ($C_{30}$) ethyl ester | 40850 | Orange |
| Canthaxanthine | 40850 | Orange |
| Acid Blue 1 | 42045 | Blue |
| 2,4-Disulfo-5-hydroxy-4''-bis(diethylamino)triphenylcarbinol | 42051 | Blue |
| 4-[(-4-N-Ethyl-p-sulfobenzylamino)phenyl-(4-hydroxy-2-sulfophenyl)(methylene)-1-(N-ethylN-p-sulfobenzyl)-2,5-cyclohexadienimine] | 42053 | Green |
| Acid Blue 7 | 42080 | Blue |
| (N-Ethyl-p-sulfobenzylamino)phenyl-(2-sulfophenyl)-methylene-(N-ethyl-N-p-sulfobenzyl)$\Delta^{2,5}$-cyclohexadienimine | 42090 | Blue |
| Acid Green 9 | 42100 | Green |
| Diethyldisulfobenzyldi-4-amino-2-chlorodi-2-methylfuchsonimmonium | 42170 | Green |
| Basic Violet 14 | 42510 | Violet |
| Basic Violet 2 | 42520 | Violet |
| 2'-Methyl-4'-(N-ethyl-N-m-sulfobenzyl)amino-4''-(N-diethyl)-amino-2-methyl-N-ethylN-m-sulfobenzylfuchsonimmonium | 42735 | Blue |
| 4'-(N-Dimethyl)amino-4''-(N-phenyl)amino-naphtho-N-di-methylfuchsonimmonium | 44045 | Blue |
| 2-Hydroxy-3,6-disulfo-4,4'-bisdimethylaminonaphtho-fuchsonimmonium | 44090 | Green |
| Acid Red 52 | 45100 | Red |
| 3-(2'-Methylphenylamino)-6-(2'-methyl-4'-sulfophenyl-amino)-9-(2''-carboxyphenyl)xanthenium salt | 45190 | Violet |
| Acid Red 50 | 45220 | Red |
| Phenyl-2-oxyfluorone-2-carboxylic acid | 45350 | yellow |
| 4,5-Dibromofluorescein | 45370 | Orange |
| 2,4,5,7-Tetrabromofluorescein | 45380 | Red |
| Solvent Dye | 45396 | Orange |
| Acid Red 98 | 45405 | Red |

-continued

| Chemical or other name | CIN | Colour |
|---|---|---|
| 3',4',5',6'-Tetrachloro-2,4,5,7-tetrabromofluorescein | 45410 | Red |
| 4,5-Diiodofluorescein | 45425 | Red |
| 2,4,5,7-Tetraiodofluorescein | 45430 | Red |
| Quinophthalone | 47000 | Yellow |
| Quinophthalonedisulfonic acid | 47005 | Yellow |
| Acid Violet 50 | 50325 | Violet |
| Acid Black 2 | 50420 | Black |
| Pigment Violet 23 | 51319 | Violet |
| 1,2-Dioxyanthraquinone, calcium/aluminium complex | 58000 | Red |
| 3-Oxypyrene-5,8,10-sulfonic acid | 59040 | Green |
| 1-Hydroxy-4-N-phenylaminoanthraquinone | 60724 | Violet |
| 1-Hydroxy-4-(4'-methylphenylamino)anthraquinone | 60725 | Violet |
| Acid Violet 23 | 60730 | Violet |
| 1,4-Di(4'-methylphenylamino)anthraquinone | 61565 | Green |
| 1,4-Bis(o-sulfo-p-toluidino)anthraquinone | 61570 | Green |
| Acid Blue 80 | 61585 | Blue |
| Acid Blue 62 | 62045 | Blue |
| N,N'-Dihydro-1,2,1',2'-anthraquinonazine | 69800 | Blue |
| Vat Blue 6; Pigment Blue 64 | 69825 | Blue |
| Vat Orange 7 | 71105 | orange |
| Indigo | 73000 | Blue |
| Indigodisulfonic acid | 73015 | Blue |
| 4,4'-Dimethyl-6,6'-dichlorothioindigo | 73360 | Red |
| 5,5'Dichloro-7,7'-dimethylthioindigo | 73385 | violet |
| Quinacridone Violet 19 | 73900 | violet |
| Pigment Red 122 | 73915 | Red |
| Pigment Blue 16 | 74100 | blue |
| Phthalocyanines | 74160 | blue |
| Direct Blue 86 | 74180 | blue |
| Chlorinated phthalocyanines | 74260 | green |
| Natural Yellow 6, 19; Natural Red 1 | 75100 | yellow |
| Bixin, Nor-Bixin | 75120 | orange |
| Lycopene | 75125 | yellow |
| trans-alpha-, -beta- or -gamma-Carotene | 75130 | orange |
| Keto and/or hydroxyl derivatives of carotene | 75135 | yellow |
| Guanine or pearlescent agent | 75170 | white |
| 1,7-Bis(4-hydroxy-3-methoxyphenyl)1,6-heptadiene-3,5-dione | 75300 | yellow |
| Complex salt (Na, Al, Ca) of carminic acid | 75470 | Red |
| Chlorophyll a and b; copper compounds of chlorophylls and chlorophyllines | 75810 | green |
| Aluminium | 77000 | white |
| Aluminium hydroxide | 77002 | white |
| Water-containing aluminium silicates | 77004 | white |
| Ultramarine | 77007 | blue |
| Pigment Red 101 and 102 | 77015 | Red |
| Barium sulfate | 77120 | white |
| Bismuth oxychloride and mixtures thereof with mica | 77163 | white |
| Calcium carbonate | 77220 | white |
| Calcium sulfate | 77231 | white |
| Carbon | 77266 | black |
| Pigment Black 9 | 77267 | black |
| Carbo medicinalis vegetabilis | 77268:1 | black |
| Chromium oxide | 77288 | green |
| Chromium oxide, water-containing | 77278 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxide | 77491 | red |
| Iron oxide hydrate | 77492 | yellow |
| Iron oxide | 77499 | black |
| Mixtures of iron(II) and iron(III) hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot 7H_2O$ | 77745 | red |
| Silver | 77820 | white |
| Titanium dioxide and mixtures thereof with mica | 77891 | white |
| Zinc oxide | 77947 | white |
| 6,7-Dimethyl-9-(1'-D-ribityl)isoalloxazine, lactoflavin | | yellow |
| Sugar dye | | brown |
| Capsanthin, capsorubin | | orange |
| Betanin | | red |
| Benzopyrylium salts, anthocyans | | red |
| Aluminium, zinc, magnesium and calcium stearate | | white |
| Bromothymol Blue | | blue |

It may furthermore be favourable to select, as dye, one or more substances from the following group: 2,4-dihydroxyazobenzene, 1-(2'-chloro-4'-nitro-1'phenylazo)-2-hydroxynaphthalene, Ceres Red, 2-(4-sulfo-1-naphthylazo)-1-naphthol-4-sulfonic acid, the calcium salt of 2-hydroxy-1,2'-azonaphthalene-1'-sulfonic acid, the calcium and barium salts of 1-(2-sulfo-4-methyl-1-phenylazo)-2-naphthylcarboxylic acid, the calcium salt of 1-(2-sulfo-1-naphthylazo)-2-hydroxynaphthalene-3-carboxylic acid, the aluminium salt of 1-(4-sulfo-1-phenylazo)-2-naphthol-6-sulfonic acid, the aluminium salt of 1-(4-sulfo-1-naphthylazo)-2-naphthol-3,6-disulfonic acid, 1-(4-sulfo-1-naphthylazo)-2-naphthol-6,8-disulfonic acid, the aluminium salt of 4-(4-sulfo-1-phenylazo)-2-(4-sulfophenyl)-5-hydroxypyrazolone-3-carboxylic acid, the aluminium and zirconium salts of 4,5-dibromofluorescein, the aluminium and zirconium salts of 2,4,5,7-tetrabromofluorescein, 3',4',5',6'-tetrachloro-2,4,5,7-tetrabromofluorescein and its aluminium salt, the aluminium salt of 2,4,5,7-tetraiodofluorescein, the aluminium salt of quinophthalonedisulfonic acid, the aluminium salt of indigodisulfonic acid, red and black iron oxide (CIN: 77 491 (red) and 77 499 (black)), iron oxide hydrate (CIN: 77492), manganese ammonium diphosphate and titanium dioxide.

Also advantageous are oil-soluble natural dyes, such as, for example, paprika extract, β-carotene or cochineal.

Also advantageous for the purposes of the present invention are gel creams comprising pearlescent pigments. Particular preference is given to the types of pearlescent pigment listed below:

1. Natural pearlescent pigments, such as, for example,
   1. "pearl essence" (guanine/hypoxanthine mixed crystals from fish scales) and
   2. "mother-of-pearl" (ground mussel shells)
2. Monocrystalline pearlescent pigments, such as, for example, bismuth oxychloride (BiOCl)
3. Layered substrate pigments: for example mica/metal oxide The basis for pearlescent pigments is formed by, for example, pulverulent pigments or castor oil dispersions of bismuth oxychloride and/or titanium dioxide as well as bismuth oxychloride and/or titanium dioxide on mica. The lustre pigment listed under CIN 77163, for example, is particularly advantageous.

Also advantageous are, for example, the following pearlescent pigment types based on mica/metal oxide:

| Group | Coating/layer thickness | Colour |
|---|---|---|
| Silver-white pearlescent pigments | $TiO_2$: 40-60 nm | silver |
| Interference pigments | $TiO_2$: 60-80 nm | yellow |
| | $TiO_2$: 80-100 nm | red |
| | $TiO_2$: 100-140 nm | blue |
| | $TiO_2$: 120-160 nm | green |
| Coloured lustre pigments | $Fe_2O_3$ | bronze |
| | $Fe_2O_3$ | copper |
| | $Fe_2O_3$ | red |
| | $Fe_2O_3$ | red-violet |

| Group | Coating/layer thickness | Colour |
|---|---|---|
| | $Fe_2O_3$ | red-green |
| | $Fe_2O_3$ | black |
| Combination pigments | $TiO_2/Fe_2O_3$ | gold shades |
| | $TiO_2/Cr_2O_3$ | green |
| | $TiO_2$/Berlin Blue | dark blue |

Particular preference is given to, for example, the pearlescent pigments available from Merck under the trade names Timiron, Colorona or Dichrona.

The list of the said pearlescent pigments is of course not intended to be limiting. Pearlescent pigments which are advantageous for the purposes of the present invention can be obtained by numerous routes known per se. For example, other substrates apart from mica can also be coated with further metal oxides, such as, for example, silica and the like. For example, $TiO_2$- and $Fe_2O_3$-coated $SiO_2$ particles ("Ronasphere" grades), which are marketed by Merck and are particularly suitable for the optical reduction of fine wrinkles, are advantageous.

It may additionally be advantageous to completely omit a substrate such as mica. Particular preference is given to pearlescent pigments prepared using $SiO_2$. Such pigments, which may additionally also have goniochromatic effects, are available, for example, from BASF under the trade name Sicopearl Fantastico.

It may also be advantageous to employ Engelhard/Mearl pigments based on calcium sodium borosilicate coated with titanium dioxide. These are available under the name Reflecks. Due to their particle size of 40-80 μm, they have a glitter effect in addition to the colour.

Also particularly advantageous are effect pigments available from Flora Tech in various colours (yellow, red, green, blue) under the trade name Metasomes Standard/Glitter. The glitter particles here are in the form of mixtures with various assistants and dyes (such as, for example, the dyes with the Colour Index (CI) numbers 19140, 77007, 77289, 77491).

The dyes and pigments can be in individual form or in the form of a mixture and mutually coated with one another, with different colour effects generally being caused by different coating thicknesses. The total amount of dyes and colouring pigments is advantageously selected from the range from, for example, 0.1% by weight to 30% by weight, preferably 0.5 to 15% by weight, in particular 1.0 to 10% by weight, in each case based on the total weight of the compositions.

All compounds or components which can be used in the compositions are either known and commercially available or can be synthesised by known processes.

The one or more compounds of the formula I can be incorporated into cosmetic or dermatological compositions in the customary manner. Suitable compositions are those for external use, for example in the form of a cream, lotion, gel or as a solution which can be sprayed onto the skin. Suitable for internal use are administration forms such as capsules, coated tablets, powders, tablet solutions or solutions.

Examples which may be mentioned of application forms of the compositions according to the invention are: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower compositions. Any desired customary vehicles, auxiliaries and, if desired, further active ingredients may be added to the composition.

Preferred auxiliaries originate from the group of the preservatives, antioxidants, stabilisers, solubilisers, vitamins, colorants, odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary vehicles, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, mascara, eyeliner, eye-shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:
  mineral oils, mineral waxes;
  oils, such as triglycerides of capric or caprylic acid, furthermore natural oils, such as, for example, castor oil;
  fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;

silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of the esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of the esters of aromatic carboxylic acids and saturated and/or unsaturated, branched and/or unbranched alcohols having a chain length of 3 to 30 C atoms. Ester oils of this type can then advantageously be selected from the group of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of the branched and unbranched hydrocarbons and wax, silicone oils, dialkyl ethers, the group of the saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18, C atoms. The fatty acid triglycerides may advantageously be selected, for example, from the group of the synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group 2-ethylhexyl isostearate, octyidodecanol, isotridecyl isononanoate, isoeicosane, 2-ethylhexyl cocoate, $C_{12-15}$-alkyl benzoate, caprylic/capric acid triglyceride and dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{2-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane or poly(methylphenylsiloxane).

Also particularly advantageous are mixtures of cyclomethicone and isotridecyl isononanoate, of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984 or 5984, in each case individually or in combination.

In particular, mixture of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions according to the invention comprise hydrophilic surfactants.

The hydrophilic surfactants are preferably selected from the group of the alkylglucosides, acyl lactylates, betaines and coconut amphoacetates.

The alkylglucosides are themselves advantageously selected from the group of the alkylglucosides which are distinguished by the structural formula

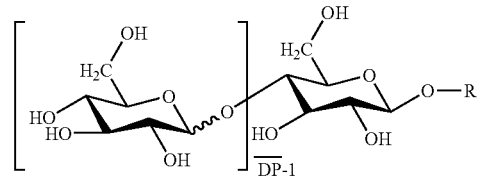

where R represents a branched or unbranched alkyl radical having 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots = \sum \frac{p_i}{100} \cdot i$$

in which $p_1, p_2, p_3 \ldots p_i$ represent the proportion of mono-, di-, tri- . . . i-fold glucosylated products in percent by weight. Advantageous in accordance with the invention is the selection of products having degrees of glucosylation of 1-2, particularly advantageously of 1.1 to 1.5, very particularly advantageously of 1.2-1.4, in particular of 1.3.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglycosides which are particularly advantageously used in accordance with the invention are selected from the group octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and auxiliaries or mixtures which are distinguished by an effective content of the active ingredients used in accordance with the invention, for example Plantaren® 1200 (Henkel KGaA), Oramix® NS 10 (Seppic).

The acyllactylates are themselves advantageously selected from the group of the substances which are distinguished by the structural formula

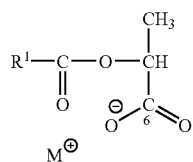

where $R^1$ denotes a branched or unbranched alkyl radical having 1 to 30 carbon atoms, and $M^+$ is selected from the group of the alkali metal ions and the group of ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group of the substances which are distinguished by the structural formula

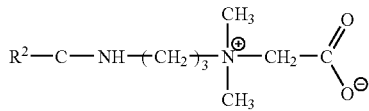

where $R^2$ denotes a branched or unbranched alkyl radical having 1 to 30 carbon atoms.

$R^2$ particularly advantageously denotes a branched or unbranched alkyl radical having 6 to 12 carbon atoms.

For example, capramidopropylbetaine, for example the product Tego® Betain 810 from Th. Goldschmidt AG, is advantageous.

A coconut amphoacetate which is advantageous in accordance with the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight preferably 0.05-10% by weight, particularly preferably 0.1-5% by weight, in each case based on the total weight of the composition.

For use, the cosmetic and dermatological compositions according to the invention are applied to the skin and/or the hair in an adequate amount in the usual manner for cosmetics.

Cosmetic and dermatological compositions according to the invention may exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous in accordance with the invention are, for example, O/W emulsifiers, principally from the group of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group of ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14)

cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:

polyethylene glycol (20) stearate, polyethylene glycol (21) stearate,
polyethylene glycol (22) stearate, polyethylene glycol (23) stearate,
polyethylene glycol (24) stearate, polyethylene glycol (25) stearate,
polyethylene glycol (12) isostearate, polyethylene glycol (13) isostearate,
polyethylene glycol (14) isostearate, polyethylene glycol (15) isostearate,
polyethylene glycol (16) isostearate, polyethylene glycol (17) isostearate,
polyethylene glycol (18) isostearate, polyethylene glycol (19) isostearate,
polyethylene glycol (20) isostearate, polyethylene glycol (21) isostearate,
polyethylene glycol (22) isostearate, polyethylene glycol (23) isostearate,
polyethylene glycol (24) isostearate, polyethylene glycol (25) isostearate,
polyethylene glycol (12) oleate, polyethylene glycol (13) oleate,
polyethylene glycol (14) oleate, polyethylene glycol (15) oleate,
polyethylene glycol (16) oleate, polyethylene glycol (17) oleate,
polyethylene glycol (18) oleate, polyethylene glycol (19) oleate,
polyethylene glycol (20) oleate, An ethoxylated alkyl ether carboxylic acid or salt thereof which can be used is advantageously sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate(cocoate.

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageously employed in accordance with the invention are the following:

fatty alcohols having 8 to 30 C atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

The preferred compositions in accordance with the invention are particularly suitable for protecting human skin against ageing processes and against oxidative stress, i.e. against damage caused by free radicals, as are produced, for example, by solar irradiation, heat or other influences. In this connection, it is in the various administration forms usually used for this application. For example, it may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which, apart from the compound(s) of the formula I or formula II, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent colour changes, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling and treating the hair, in the form of a lotion or gel for brushing or blow-waving, in the form of a hair lacquer, permanent waving composition, colorant or bleach for the hair. Besides the compound(s) of the formula I or formula II, the composition having light-protection properties may comprise various adjuvants used in this type of composition, such as surface-active agents, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The present invention furthermore relates to a process for the preparation of a composition which is characterised in that at least one compound of the formula I or formula II having radicals as described above is mixed with a vehicle which is suitable cosmetically or dermatologically or for foods, and to the use of a compound of the formula I or formula II for the preparation of a composition.

The compositions according to the invention can be prepared using techniques which are well known to the person skilled in the art.

The mixing can result in dissolution, emulsification or dispersion of the compound of the formula I or formula II in the vehicle.

It has also been noted that compounds of the formula I or formula II can have a stabilising effect on the composition. When used in corresponding products, the latter thus also remain stable for longer and do not change their appearance. In particular, the effectiveness of the ingredients, for example vitamins, is retained even in the case of application over extended periods or extended storage. This is, inter alia, particularly advantageous in the case of compositions for protecting the skin against the effect of UV rays since these cosmetics are exposed to particularly high stresses by UV radiation.

The present invention furthermore relates to a process for the preparation of a composition which is characterised in that at least one compound of the formula I having radicals as described above is mixed with a cosmetically or dermatologically suitable vehicle, and to the use of a compound of the formula I for the preparation of a composition having light-protection properties.

The compositions according to the invention can be prepared using techniques which are well known to the person skilled in the art.

The mixing can result in dissolution, emulsification or dispersion of the compound of the formula I in the vehicle.

In a process which is preferred in accordance with the invention, the compound of the formula II is prepared by reaction of a 2-hydroxyacetophenone compound with a lithium compound and subsequently with a keto compound. The preparation of these compounds is described in EP-A-1382329 and WO2002060889A1, the relevant disclosure content of which expressly also belongs to the disclosure content of the present application.

The complex compounds of the formula I can be prepared by reacting compounds of the formula II with cyclodextrins in solution, preferably at elevated temperature. The present invention furthermore relates to a corresponding process.

It has been found that, in preferred embodiments of the present invention, complexes containing about 1 or 2 mol of cyclodextrin per mole of flavonoid of the formula II meet the requirements according to the invention in a particular manner. It is therefore preferred in accordance with the invention for o in formula I to be equal to 1 and p to be in the range 1 to 3, preferably for p to be in the range 1.7 to 2.1.

Corresponding compounds can be prepared if the cyclodextrin is employed in excess or precisely in the molar ratio 1:1 or 2:1 relative to the flavonoid.

It has also been noted that compounds of the formula I can have a stabilising effect on the composition. When used in corresponding products, the latter thus also remain stable for longer and do not change their appearance. In particular, the effectiveness of the ingredients, for example vitamins, is retained even in the case of application over extended periods or extended storage. This is particularly advantageous in the case of compositions for protecting the skin against the effect of UV rays since these cosmetics are exposed to particularly high stresses by UV radiation.

The antioxidant action of the compounds of the formula I can be demonstrated, for example, by means of 2,2-diphenyl-1-picrylhydrazyl (DPPH) assay. 2,2-Diphenyl-1-picrylhydrazyl is a free radical which is stable in solution. The unpaired electron results in a strong absorption band at 515 nm, and the solution has a dark violet colour. In the presence of a free-radical scavenger, the electron is paired, the absorption disappears, and the decolouration proceeds stoichiometrically taking into account the electrons taken up. The absorbance is measured in a photometer. The anti-free-radical property of the substance to be tested is determined by measuring the concentration at which 50% of the 2,2-diphenyl-1-picrylhydrazyl employed has reacted with the free-radical scavenger. This concentration is expressed as $EC_{50}$, a value which can be considered to be a property of the substance under the given measurement conditions. The substance investigated is compared with a standard (for example tocopherol).

The evaluation is carried out graphically by plotting the test substance/DPPH molar ratio against the percentage drop in absorbance and determining the $EC_{50}$ by reading off at 50%. In addition, the slope of the lines in the linear region is determined and the $EC_{50}$ is calculated.

The positive effects of compounds of the formula I give rise to their particular suitability for use in cosmetic or pharmaceutical compositions.

The properties of compounds of the formula I should likewise be regarded as positive for use in foods or as food supplements or as functional foods. The further explanations given for foods also apply correspondingly to food supplements and functional food.

The foods which can be enriched with one or more compounds of the formula I in accordance with the present invention include all materials which are suitable for consumption by animals or consumption by humans, for example vitamins and provitamins thereof, fats, minerals or amino acids. (The foods may be solid, but also liquid, i.e. in the form of a beverage).

Foods which can be enriched with one or more compounds of the formula I accordance with the present invention are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched with one or more compounds of the formula I or formula II in accordance with the present invention are corn or cereals from a single plant species and materials produced from plant species of this type, such as, for example, cereal syrup, rye flour, wheat flour or oat bran. Mixtures of foods of this type are also suitable for being enriched with one or more compounds of the formula I in accordance with the present invention, for example multivitamin preparations, mineral mixtures or sweetened juice. As further examples of foods which can be enriched with one or more compounds of the formula I in accordance with the present invention, mention may be made of food compositions, for example prepared cereals, biscuits, mixed drinks, foods prepared especially for children, such as yoghurt, diet foods, low-calorie foods or animal feeds.

The foods which can be enriched with one or more compounds of the formula I in accordance with the present invention thus include all edible combinations of carbohydrates, lipids, proteins, inorganic elements, trace elements, vitamins, water or active metabolites of plants and animals.

The foods which can be enriched with one or more compounds of the formula I in accordance with the present invention are preferably administered orally, for example in the form of meals, pills, tablets, capsules, powders, syrup, solutions or suspensions.

The foods according to the invention enriched with one or more compounds of the formula I can be prepared using techniques which are well known to the person skilled in the art.

Due to their action as antioxidants or free-radical scavengers, compounds of the formula I are also suitable as medicament ingredient, where they support or replace natural mechanisms which scavenge free radicals in the body action. The compounds of the formula I can in some cases be compared in their action with free-radical scavengers, such as vitamin C. Compounds of the formula I can be used, for example, for the preventative treatment of inflammation and allergies of the skin and in certain cases for preventing certain types of cancer. Compounds of the formula I are particularly suitable for the preparation of a medicament for the treatment of inflammation, allergies and irritation, in particular of the skin. It is furthermore possible to prepare medicaments which act as vein tonic, as agent foras chemical, physical or actinic erythema inhibitor, as agents for increasing the strength of blood capillaries, as cuperose inhibitor, as inhibitor of chemical, physical or actinic erythemas, as agent for the treatment of sensitive skin, as decongestant, as dehydration agent, as slimming agent, as anti-wrinkle agent, as stimulators for the synthesis of components of the extracellular matrix, as strengthening agent for improving skin elasticity, and as anti-ageing agent. Furthermore, compounds of the formula I which are preferred in this connection exhibit anti-allergic and anti-inflammatory and anti-irritative actions. They are therefore suitable for the preparation of medicaments for the treatment of inflammation or allergic reactions.

The invention furthermore relates, as already mentioned above, to the stabilisation of UV filters. A known and high-performance class of light-protection filter substances is formed by the dibenzoylmethane derivatives. However, it is disadvantageous that these substances are decomposed very easily by UV light and thus lose their protective properties. As an example of a light-protection filter from this class of compounds which is available on the market, mention may be made of 4-(tert-butyl)-4'-methoxydibenzoylmethane, which has the structure shown below.

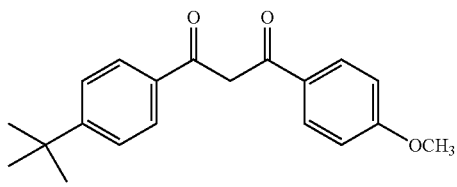

Surprisingly, it has now been found that compounds of the formula I have a stabilising action for the dibenzoylmethanes, in particular 4-(tert-butyl)-4-methoxybenzoylmethane. By incorporating mixtures of these compounds into cosmetics, it is now possible to use dibenzoylmethanes for the preparation of light-protection compositions which have only a slight reduction in the protective action against UV rays, or none at all, even on extended exposure to the sun, for example during sunbathing for a number of hours.

The invention is explained in greater detail below with reference to examples.

EXAMPLES

Example A

Preparation of a 7,4'-dihydroxyflavone/cyclodextrin Complex (3.1 g, 4.72 mmol) of hydroxypropyl-gamma-cyclodextrin (Aldrich; 2'-hydroxypropylcyclooctaamylose; Cas. No. 128446-34-4) are initially introduced in 70 ml of water and warmed to 50° C. 0.3 g of 7,4'-dihydroxyflavone is dissolved in 60 ml of ethanol and added dropwise to the initially introduced solution. The solution is stirred overnight at 50° C. The ethanol is distilled off from the solution. The residue is evaporated to dryness in vacuo, and the solid which remains is dried overnight at 40° C. and 200 mbar.

Cyclodextrin complexes of
6,3',4'-trihydroxyflavone
5,6,7-trihydroxyflavone
7,8,3',4'-tetrahydroxyflavone
7,8-dihydroxy-3',4'-dimethoxyflavone
7,4'-dihydroxyflavone
7-hydroxy-4'-methoxyflavone
6-hydroxy-4'-methoxyflavone
6,4'-dihydroxyflavone
6,7-dihydroxyflavone
6,7-dihydroxy-3',4',5'-trimethoxyflavone
7-glucose-4'-methoxyflavone
4'-methoxy-6-hydroxyflavone
4'-methoxy-7-hydroxyflavone
are obtained analogously to Example A.

In the following example formulations 1 to 6, 4'-methoxy-6-hydroxyflavone is in each case employed as 4'-methoxy-6- hydroxyflavone/hydroxypropyl-gamma-cyclodextrin complex in accordance with Example A.

Example 1

Lotion (W/O) for Application to the Skin

|   |   | % by wt. |
|---|---|---|
| A | Polyglyceryl 2-dipolyhydroxystearate | 5.0 |
|   | Beeswax | 0.5 |
|   | Zinc stearate | 0.5 |
|   | Hexyl laurate | 9.0 |
|   | Cetyl isononanoate | 6.0 |
|   | Shea butter | 0.5 |
|   | DL-α-Tocopherol acetate | 1.0 |
|   | 4'-Methoxy-6-hydroxyflavone | 0.5 |
| B | Glycerin | 5.0 |
|   | Magnesium sulfate heptahydrate | 1.0 |
|   | Preservatives | q.s. |
|   | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The preservatives used are the following:

0.05% of propyl 4-hydroxybenzoate 0.15% of methyl 4-hydroxybenzoate

Example 2

Lotion (W/O) for Application to the Skin

|   |   | % by wt. |
|---|---|---|
| A | Polyglyceryl 2-dipolyhydroxystearate | 5.0 |
|   | Beeswax | 0.5 |
|   | Zinc stearate | 0.5 |
|   | Hexyl laurate | 9.0 |
|   | Cetyl isononanoate | 6.0 |
|   | Shea butter | 0.5 |
|   | DL-α-Tocopherol acetate | 1.0 |
| B | 4'-Methoxy-6-hydroxyflavone | 1.0 |
|   | Glycerin | 5.0 |
|   | Magnesium sulfate heptahydrate | 1.0 |
|   | Preservatives | q.s. |
|   | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The preservatives used are the following:

0.05% of propyl 4-hydroxybenzoate 0.15% of methyl 4-hydroxybenzoate

Example 3

Lotion (W/O) for Application to the Skin

|   |   | % by wt. |
|---|---|---|
| A | 4,6,3',4'-Tetrahydroxybenzylcoumaranone-3 | 1.0 |
|   | Polyglyceryl 2-dipolyhydroxystearate | 5.0 |
|   | Beeswax | 0.5 |
|   | Zinc stearate | 0.5 |
|   | Hexyl laurate | 9.0 |
|   | Cetyl isononanoate | 6.0 |
|   | Shea butter | 0.5 |
|   | DL-α-Tocopherol acetate | 1.0 |
|   | 4'-Methoxy-6-hydroxyflavone | 1.0 |
| B | Glycerin | 5.0 |
|   | Magnesium sulfate heptahydrate | 1.0 |
|   | Preservatives | q.s. |
|   | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The preservatives used are the following:

0.05% of propyl 4-hydroxybenzoate 0.15% of methyl 4-hydroxybenzoate

Example 4

A cream (O/W) comprising ectoin is prepared from the following components:

|   |   |   | % by wt. |
|---|---|---|---|
| A | Paraffin, liquid | (1) | 8.0 |
|   | Isopropyl myristate | (1) | 4.0 |
|   | Mirasil CM5 | (2) | 3.0 |
|   | Stearic acid | (1) | 3.0 |
|   | Arlacel 165 V | (3) | 5.0 |
|   | 4'-Methoxy-6-hydroxyflavone |  | 1.0 |
| B | Glycerin (87%) | (1) | 3.0 |
|   | Germaben II | (4) | 0.5 |
|   | Water, demineralised |  | to 100 |
| C | RonaCare ™ ectoin | (1) | 1.0 |

Preparation

Firstly, phases A and B are warmed separately to 75° C. Phase A is then slowly added to phase B with stirring, and stirring is continued until a homogeneous mixture has formed. After homogenisation, the emulsion is cooled to 30° C. with stirring. The mixture is subsequently warmed to 35° C., phase C is added, and the mixture is stirred to homogeneity.

Sources of Supply (1) Merck KGaA (2) Rhodia (3) Uniqema (4) ISP

Example 5

Topical Composition as W/O Emulsion

|   |                          |     | % by wt. |
|---|--------------------------|-----|----------|
| A | Isolan PDI               | (2) | 3.0      |
|   | Paraffin oil, liq.       | (1) | 17.0     |
|   | Isopropyl myristate      |     | 5.0      |
|   | Beeswax                  |     | 0.2      |
|   | Cutina HR                | (2) | 0.3      |
|   | 4'-Methoxy-6-hydroxyflavone |  | 1.0      |
| B | Water, demineralised     |     | to 100   |
|   | Glycerin (87%)           |     | 4.0      |
|   | Magnesium sulfate        |     | 1.0      |
|   | Germaben II-E            | (3) | 1.0      |
| C | RonaCare ™ LPO           | (1) | 2.0      |

Preparation

Phases A and B are warmed to 75° C. Phase B is added to phase A with stirring. The mixture is subsequently homogenised for 2 min. using the Turrax at 9000 rpm. The mixture obtained is cooled to 30 to 35° C., and C is stirred in.

Sources of Supply (1) Merck KGaA
(2) Goldschmidt AG
(3) ISP

Example 6

Pump Spray

|                              | % by wt. |
|------------------------------|----------|
| 4'-Methoxy-6-hydroxyflavone  | 1.0      |
| Ethanol 96%                  | 40.0     |
| PEG-20 glyceryl laurate      | 7.0      |
| 1,2-Propanediol              | 5.0      |
| Water, demineralised         | to 100   |

Preparation

Lueolin-CD is dissolved in water, and the remaining constituents are added with stirring.

Example 7

Compositions

Formulations of cosmetic compositions which comprise the flavonoid/2-hydroxypropyl-gamma-cyclodextrin complexes according to Examples A are indicated by way of example below, with only the flavonoid name being employed in each case in the tables. In addition, the INCI names of the commercially available compounds are indicated.

UV-Pearl, OMC stands for the composition having the INCI name:

Water (for EU: Aqua), Ethylhexyl Methoxycinnamate, Silica, PVP, Chlorphenesin, BHT; this composition is commercially available from Merck KGaA, Darmstadt, under the name Eusolex®UV Pearl™OMC.

The other UV-Pearls indicated in the tables each have an analogous composition, with OMC being replaced by the UV filters indicated.

TABLE 1

| W/O emulsions (data in % by weight) | | | | | | | | | | |
|---|---|---|---|---|---|---|---|---|---|---|
|  | 1-1 | 1-2 | 1-3 | 1-4 | 1-5 | 1-6 | 1-7 | 1-8 | 1-9 | 1-10 |
| Titanium dioxide |  | 2 | 5 |  |  |  |  |  |  | 3 |
| 4'-Methoxy-7-hydroxyflavone | 5 | 3 | 2 | 1 | 2 |  |  |  | 1 | 1 |
| 4'-Methoxy-6-hydroxyflavone |  |  |  |  |  | 1 | 2 | 1 |  |  |
| Zinc oxide |  |  |  |  |  |  |  | 5 | 2 |  |
| UV-Pearl, OMC | 30 | 15 | 15 | 15 | 15 | 15 | 15 | 15 | 15 | 15 |
| Polyglyceryl-3-Dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 | to 100 |

|  | 1-11 | 1-12 | 1-13 | 1-14 | 1-15 | 1-16 | 1-17 | 1-18 |
|---|---|---|---|---|---|---|---|---|
| Titanium dioxide | 3 |  | 2 |  | 3 |  | 2 | 5 |
| Benzylidene malonate polysiloxane |  | 1 | 0.5 |  |  |  |  |  |
| Methylene Bis-Benztriazolyl Tetramethylbutylphenol |  | 1 | 0.5 | 1 |  |  |  |  |

TABLE 1-continued

W/O emulsions (data in % by weight)

| | | | | | | | | |
|---|---|---|---|---|---|---|---|---|
| 4',7-Dihydroxyflavone | 5 | 3 | 2 | 5 | 1 | 3 | 7 | 2 |
| Polyglyceryl-3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Dicocoyl Pentyerythrityl Citrate (and) Sorbitan Sesquioleate (and) Cera Alba (and) Aluminium Stearate | | | | | 6 | 6 | 6 | 6 |
| PEG-7 Hydrogenated Castor Oil | | | | | 1 | 1 | 1 | 1 |
| Zinc Stearate | | | | | 2 | 2 | 2 | 2 |
| Oleyl Erucate | | | | | 6 | 6 | 6 | 6 |
| Decyl Oleate | | | | | 6 | 6 | 6 | 6 |
| Dimethicone | | | | | 5 | 5 | 5 | 5 |
| Tromethamine | | | | | 1 | 1 | 1 | 1 |
| Glycerin | | | | | 5 | 5 | 5 | 5 |
| Allantoin | | | | | 0.2 | 0.2 | 0.2 | 0.2 |
| Water | to 100 | to 100 | to 100 | to 100 | to 100 | to 100 | to 100 | to 100 |

| | 1-19 | 1-20 | 1-21 | 1-22 | 1-23 | 1-24 | 1-25 | 1-26 | 1-27 | 1-28 | 1-29 |
|---|---|---|---|---|---|---|---|---|---|---|---|
| Titanium dioxide | | 2 | 5 | | | | | | | 3 | 3 |
| Benzylidene malonate polysiloxane | | | | 1 | | | | | 1 | 1 | |
| Methylene Bis-Benztriazolyl Tetramethylbutylphenol | | | | | 1 | 2 | 1 | | | | 1 |
| Zinc oxide | | | | | | | | 5 | 2 | | |
| UV-Pearl OMC | 5 | 5 | 5 | 5 | 7 | 5 | 5 | 5 | 5 | 5 | 8 |
| UV-Pearl, OCR | | 10 | | | | | | | | | 5 |
| UV-Pearl, EthylhexylDimethylPABA | | | 10 | | | | | | | | |
| UV-Pearl, Homosalate | | | | 10 | | | | | | | |
| UV-Pearl, Ethylhexyl salicylate | | | | | 10 | | | | | | |
| UV-Pearl, OMC, BP-3 | | | | | | 10 | | | | | |
| UV-Pearl, OCR, BP-3 | | | | | | | 10 | | | | |
| UV-Pearl, Ethylhexyl Dimethyl PABA, BP-3 | | | | | | | | 10 | | | |
| UV-Pearl, Homosalate, BP-3 | | | | | | | | | 10 | | |
| UV-Pearl, Ethylhexyl salicylate, BP-3 | | | | | | | | | | 10 | |
| BMDBM | | | | | | | | | | | 2 |
| UV-Pearl OMC, 4-Methyl-benzylidene Camphor | 25 | | | | | | | | | | |
| Polyglyceryl-3-Dimerate | 3 | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 | 0.5 |
| Propylparabene | 0.05 | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 | 0.15 |
| Water | | | | | | to 100 | | | | | |

TABLE 2

O/W emulsions, data in % by weight

| | 2-1 | 2-2 | 2-3 | 2-4 | 2-5 | 2-6 | 2-7 | 2-8 | 2-9 | 2-10 |
|---|---|---|---|---|---|---|---|---|---|---|
| Titanium dioxide | | 2 | 5 | | | | | | 3 | |
| Methylene Bis-Benztriazolyl Tetramethylbutylphenol | | | | | | 1 | 2 | 1 | | |
| 4'-Methoxy-7-β-glucosidylflavone | | | | 1 | 2 | | | | 1 | 1 |

TABLE 2-continued

O/W emulsions, data in % by weight

| | 2-1 | 2-2 | 2-3 | 2-4 | 2-5 | 2-6 | 2-7 | 2-8 | 2-9 | 2-10 |
|---|---|---|---|---|---|---|---|---|---|---|
| 4'-Methoxy-6-hydroxyflavone | 1 | 3 | | 2 | | 5 | | 5 | 2 | |
| 4'-Methoxy-7-hydroxyflavone | 5 | 5 | 5 | 5 | 5 | 5 | 5 | 5 | 5 | 5 |
| 4',7-Dihydroxyflavone | 1 | 5 | 4 | | 6 | | 7 | | 2 | 1 |
| 4-Methylbenzylidene Camphor | 2 | | 3 | | 4 | | 3 | | 2 | |
| BMDBM | 1 | 3 | | 3 | 3 | | 3 | 3 | 3 | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE | | | | | | | | | | |
| Stearic Acid | | | | | | | | | | |
| Persea Gratissima | | | | | | | | | | |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Tromethamine | | | 1.8 | | | | | | | |
| Glycerin | | | | | | | | | | |
| Water | to 100 | to 100 | to 100 | to 100 | to 100 | to 100 | to 100 | to 100 | to 100 | to 100 |

| | 2-11 | 2-12 | 2-13 | 2-14 | 2-15 | 2-16 | 2-17 | 2-18 |
|---|---|---|---|---|---|---|---|---|
| Titanium dioxide | | 3 | | 2 | | | 2 | 5 |
| Benzylidene malonate polysiloxane | | | 1 | 0.5 | | | | |
| Methylene Bis-Benztriazolyl Tetramethylbutylphenol | | 1 | 1 | 0.5 | | | | |
| 4'-Methoxy-7-β-glucosidylflavone | | | | | 1 | 2 | | |
| 4'-Methoxy-6-hydroxyflavone | | 1 | 3 | | 2 | | 5 | 5 |
| 4'-Methoxy-7-hydroxyflavone | 5 | 5 | 5 | 5 | 5 | 5 | 5 | 5 |
| 4',7-Dihydroxyflavone | 1 | 5 | 4 | | 6 | | 7 | |
| Zinc oxide | | | | 2 | | | | |
| UV-Pearl, OMC | 15 | 15 | 15 | 30 | 30 | 30 | 15 | 15 |
| 4-Methylbenzylidene Camphor | | | | 3 | | | | |
| BMDBM | | | | 1 | | | | |
| Phenylbenzimidazole Sulfonic Acid | | | | | 4 | | | |
| Stearyl Alcohol (and) Steareth-7 (and) Steareth-10 | 3 | 3 | 3 | 3 | | | | |
| Glyceryl Stearate (and) Ceteth-20 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |
| Oleyl Oleate | 6 | 6 | 6 | 6 | | | | |
| Propylene Glycol | 4 | 4 | 4 | 4 | | | | |
| Glyceryl Stearate SE | | | | | 6 | 6 | 6 | 6 |
| Stearic Acid | | | | | 2 | 2 | 2 | 2 |
| Persea Gratissima | | | | | 8 | 8 | 8 | 8 |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Tromethamine | | | | | 1.8 | | | |
| Glycerin | | | | | | 3 | 3 | 3 |
| Water | to 100 | to 100 | to 100 | to 100 | to 100 | to 100 | to 100 | to 100 |

| | 2-19 | 2-20 | 2-21 | 2-22 | 2-23 | 2-24 | 2-25 | 2-26 | 2-27 | 2-28 |
|---|---|---|---|---|---|---|---|---|---|---|
| Titanium dioxide | | | | | | | 3 | 3 | | 2 |
| Benzylidene malonate polysiloxane | 1 | 2 | | | | 1 | 1 | | 1 | 0.5 |
| 4'-Methoxy-7-β-glucosidylflavone | | | 1 | | 2 | | | | 1 | 1 |
| 4'-Methoxy-6-hydroxyflavone | 1 | 3 | | 2 | | 5 | | 5 | 2 | |
| 4'-Methoxy-7-hydroxyflavone | 5 | 5 | 5 | 5 | 5 | 5 | 5 | 5 | 5 | 5 |
| 4',7-Dihydroxyflavone | 1 | 5 | 4 | | 6 | | 7 | | 2 | 1 |
| Methylene Bis-Benztriazolyl Tetramethylbutylphenol | | | 1 | 2 | 1 | | | 1 | 1 | 0.5 |
| Zinc oxide | | | | | 5 | 2 | | | | 2 |
| UV-Pearl, OMC | 15 | 15 | 15 | 15 | 15 | 15 | 15 | 15 | 15 | 15 |
| Caprylic/Capric Triglyceride | 14 | 14 | 14 | 14 | 14 | 14 | 14 | 14 | 14 | 14 |
| Oleyl Oleate | | | | | | | | | | |
| Propylene Glycol | | | | | | | | | | |
| Glyceryl Stearate SE | 6 | 6 | 6 | 6 | 6 | 6 | 6 | 6 | 6 | 6 |

TABLE 2-continued

| O/W emulsions, data in % by weight | | | | | | | | | | |
|---|---|---|---|---|---|---|---|---|---|---|
| Stearic Acid | 2 | 2 | 2 | 2 | 2 | 2 | 2 | 2 | 2 | 2 |
| Persea Gratissima | 8 | 8 | 8 | 8 | 8 | 8 | 8 | 8 | 8 | 8 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Glyceryl Stearate, Ceteareth-20, Ceteareth-10, Cetearyl Alcohol, Cetyl Palmitate | | | | | | | | | | |
| Ceteareth-30 | | | | | | | | | | |
| Dicaprylyl Ether | | | | | | | | | | |
| Hexyldecanol, Hexyldexyllaurate | | | | | | | | | | |
| Cocoglycerides | | | | | | | | | | |
| Tromethamine | | | | | | | | | | |
| Glycerin | 3 | 3 | 3 | 3 | 3 | 3 | 3 | 3 | 3 | 3 |
| Water | to 100 | to 100 | to 100 | to 100 | to 100 | to 100 | to 100 | to 100 | to 100 | to 100 |

TABLE 3

| Gels, data in % by weight | | | | | | | | | | |
|---|---|---|---|---|---|---|---|---|---|---|
| | 3-1 | 3-2 | 3-3 | 3-4 | 3-5 | 3-6 | 3-7 | 3-8 | 3-9 | 3-10 |
| a = aqueous gel | | | | | | | | | | |
| Titanium dioxide | | 2 | 5 | | | | | | | 3 |
| 4'-Methoxy-7-β-glucosidylflavone | | | | 1 | 2 | | | | 1 | 1 |
| 4'-Methoxy-6-hydroxyflavone | 1 | 3 | | 2 | | 5 | | 5 | 2 | |
| 4'-Methoxy-7-hydroxyflavone | 5 | 5 | 5 | 5 | 5 | 5 | 5 | 5 | 5 | 5 |
| 4',7-Dihydroxyflavone | 1 | 5 | 4 | | 6 | | 7 | | 2 | 1 |
| Benzylidene malonate polysiloxane | | | 1 | 1 | 2 | | | | 1 | 1 |
| Methylene Bis-Benztriazolyl Tetramethylbutylphenol | | 1 | | | | 1 | 2 | 1 | | |
| Zinc oxide | | | | 2 | | | | 5 | 2 | |
| UV-Pearl, Ethylhexyl Mehtoxycinnamat | 30 | 15 | 15 | 15 | 15 | 15 | 15 | 15 | 15 | 15 |
| 4-Methylbenzylidene Camphor | | | | | 2 | | | | | |
| Butylmethoxydibenzoylmethane | | 1 | | | | | | | | |
| Phenylbenzimidazole Sulfonic Acid | | | 4 | | | | | | | |
| Prunus Dulcis | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

| | 3-11 | 3-12 | 3-13 | 3-14 | 3-15 | 3-16 | 3-17 | 3-18 |
|---|---|---|---|---|---|---|---|---|
| a = aqueous gel | | | | a | a | a | a | a |
| Titanium dioxide | | 3 | | 2 | | | | |
| Benzylidene malonate polysiloxane | | 1 | 0.5 | 1 | 2 | | | |
| Methylene Bis-Benztriazolyl Tetramethylbutylphenol | 1 | 1 | 0.5 | | | 1 | 2 | 1 |
| 4'-Methoxy-7-β-glucosidylflavone | | | | 1 | 2 | | | |
| 4'-Methoxy-6-hydroxyflavone | 1 | 3 | | 2 | | 5 | | 5 |
| 4'-Methoxy-7-hydroxyflavone | 5 | 5 | 5 | 5 | 5 | 5 | 5 | 5 |
| 4',7-Dihydroxyflavone | 1 | 5 | 4 | | 6 | | 7 | |
| Zinc oxide | | | 2 | | | | | |
| UV-Pearl, Ethylhexyl Mehtoxycinnamat | 15 | 15 | 15 | 15 | 15 | 15 | 15 | 15 |
| Prunus Dulcis | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |

TABLE 3-continued

Gels, data in % by weight

| | | | | | | | | |
|---|---|---|---|---|---|---|---|---|
| PEG-8 (and) Tocopherol (and) Ascorbyl Palmitate (and) Ascorbic Acid (and) Citric Acid | 0.05 | 0.05 | 0.05 | | | | | |
| Sorbitol | 4 | 4 | 4 | 5 | 5 | 5 | 5 | 5 |
| Polyacrylamide (and) C13-14 Isoparaffin (and) Laureth-7 | 3 | 3 | 3 | | | | | |
| Carbomer | | | | 1.5 | 1.5 | 1.5 | 1.5 | 1.5 |
| Propylparabene | 0.05 | 0.05 | 0.05 | | | | | |
| Methylparabene | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | to 100 | to 100 | to 100 | to 100 | to 100 | to 100 | to 100 | to 100 |

| | 3-19 | 3-20 | 3-21 | 3-22 | 3-23 | 3-24 | 3-25 | 3-26 | 3-27 | 3-28 |
|---|---|---|---|---|---|---|---|---|---|---|
| 4'-Methoxy-7-β-glucosidyl-flavone | | | | 1 | 2 | | | | 1 | 1 |
| 4'-Methoxy-6-hydroxyflavone | 1 | 3 | | 2 | | 5 | | 5 | 2 | |
| 4'-Methoxy-7-hydroxyflavone | 5 | 5 | 5 | 5 | 5 | 5 | 5 | 5 | 5 | 5 |
| 4',7-Dihydroxyflavone | 1 | 5 | 4 | | 6 | | 7 | | 2 | 1 |
| UV-Pearl, OMC | 30 | 30 | 15 | 15 | 15 | 11 | 12 | 15 | 15 | 15 |
| Phenylbenzimidazole Sulfonic Acid | | 4 | 4 | | | | | | | |
| Sorbitol | 5 | 5 | 5 | 5 | 5 | 5 | 5 | 5 | 5 | 5 |
| Carbomer | 1.5 | 1.5 | 1.5 | 1.5 | 1.5 | 1.5 | 1.5 | 1.5 | 1.5 | 1.5 |
| Propylparabene | | | | | | | | | | |
| Methylparabene | 0.15 | 0.15 | 0.15 | 0.15 | 0.15 | 0.15 | 0.15 | 0.15 | 0.15 | 0.15 |
| Allantoin | 0.2 | 0.2 | 0.2 | 0.2 | 0.2 | 0.2 | 0.2 | 0.2 | 0.2 | 0.2 |
| Tromethamine | 2.4 | 4.2 | 4.2 | 2.4 | 2.4 | 2.4 | 2.4 | 2.4 | 2.4 | 2.4 |
| Water | to 100 | to 100 | to 100 | to 100 | to 100 | to 100 | to 100 | to 100 | to 100 | to 100 |

| | 3-29 | 3-30 | 3-31 | 3-32 | 3-33 | 3-34 | 3-35 | 3-36 |
|---|---|---|---|---|---|---|---|---|
| 4'-Methoxy-7-β-glucosidflavone | | | | 1 | 2 | | | |
| 4'-Methoxy-6-hydroxyflavone | 1 | 3 | | 2 | | 5 | | 5 |
| 4'-Methoxy-7-hydroxyflavone | 5 | 5 | 5 | 5 | 5 | 5 | 5 | 5 |
| 4',7-Dihydroxyflavone | 1 | 5 | 4 | | 6 | | 7 | |
| UV-Pearl, OMC | 15 | 10 | | 10 | 10 | 10 | 15 | 10 |
| UV-Pearl, OCR | | | 10 | | | | | |
| UV-Pearl, OMC, Methylene Bis-Benztriazolyl Tetramethylbutylphenol | | 7 | | 6 | | | | |
| UV-Pearl, Ethylhexyl salicylate, BMDBM | | | 10 | | | | | |
| Disodium Phenyl Dibenzimidazole Tetrasulfonate | | 3 | | | | 3 | | 3 |
| Phenylbenzimidazole Sulfonic Acid | | 2 | | | 2 | 3 | | 3 |
| Prunus Dulcis | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |
| PEG-8 (and) Tocopherol (and) Ascorbyl Palmitate (and) Ascorbic Acid (and) Citric Acid | 0.05 | 0.05 | 0.05 | | | | | |
| Sorbitol | 4 | 4 | 4 | 5 | 5 | 5 | 5 | 5 |
| Polyacrylamide (and) C13-14 Isoparaffin (and) Laureth-7 | 3 | 3 | 3 | | | | | |
| Carbomer | | | | 1.5 | 1.5 | 1.5 | 1.5 | 1.5 |
| Propylparabene | 0.05 | 0.05 | 0.05 | | | | | |
| Methylparabene | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | — 100 | — 100 | — 100 | — 100 | — 100 | — 100 | — 100 | — 100 |

The invention claimed is:
1. A compound of formula I

[Structure of formula I: a flavone skeleton with substituents $R^1$ through $R^{10}$, shown in brackets with [CD]$_p$]

where
$R^1$ and $R^2$ are
H,
OR$^{11}$, where each OR$^{11}$, independently of the others, stands for
OH,
a straight-chain or branched $C_1$- to $C_{20}$-alkoxy group,
a straight-chain or branched $C_3$- to $C_{20}$-alkenyloxy group,
a straight-chain or branched $C_1$- to $C_{20}$-hydroxyalkoxy group, where the hydroxyl group(s) may be bonded to a primary or secondary carbon atom in the chain and furthermore the alkyl chain may also be interrupted by oxygen,
a $C_3$- to $C_{10}$-cycloalkoxy group or $C_3$- to $C_{12}$-cycloalkenyloxy group, where the rings may each also be bridged by —(CH$_2$)$_n$— groups, where n=1 to 3, or
a mono- and/or oligoglycosyl radical,
with the proviso that at least one radical from $R^1$ and $R^2$ stands for OR$^{11}$ and
$R^3$ to $R^{10}$ may be identical or different and each stands, independently of one another, for
H,
OR$^{11}$,
a straight-chain or branched $C_1$- to $C_{20}$-alkyl group,
a straight-chain or branched $C_3$- to $C_{20}$-alkenyl group,
a straight-chain or branched $C_1$- to $C_{20}$-hydroxyalkyl group, where the hydroxyl group may be bonded to a primary or secondary carbon atom in the chain and furthermore the alkyl chain may also be interrupted by oxygen, or
a $C_3$- to $C_{10}$-cycloalkyl group or $C_3$- to $C_{12}$-cycloalkenyl group, where the rings may each also be bridged by —(CH$_2$)$_n$— groups, where n=1 to 3,
CD stands for hydroxypropyl-gamma-cyclodextrin,
o stands for the number 1, and
p stands for a number from the range 0.5 to 50.
2. A compound according to claim 1, wherein $R^4$ to $R^7$ and $R^{10}$ may be identical or different and each stands, independently of one another, for
H,
a straight-chain or branched $C_1$- to $C_{20}$-alkyl group,
a straight-chain or branched $C_3$- to $C_{20}$-alkenyl group,
a straight-chain or branched $C_1$- to $C_{20}$-hydroxyalkyl group, where the hydroxyl group may be bonded to a primary or secondary carbon atom in the chain and furthermore the alkyl chain may also be interrupted by oxygen, or
a $C_3$- to $C_{10}$-cycloalkyl group or $C_3$- to $C_{12}$-cycloalkenyl group, where the rings may in each case also be bridged by —(CH$_2$)$_n$-groups, where n=1 to 3.
3. A compound according to claim 1, wherein $R^4$ to $R^7$ and $R^{10}$ are H.
4. A compound according to claim 1, wherein $R^3$ stands for OH,
a straight-chain or branched $C_1$- to $C_{20}$-alkoxy group, or
a mono- and/or oligoglycosyl radical.
5. A compound according to claim 1, wherein $R^3$ stands for a straight-chain or branched $C_1$- to $C_{20}$-alkoxy group, and $R^8$ and $R^9$ are identical and stand for H or straight-chain or branched $C_1$- to $C_{20}$-alkoxy groups.
6. A compound according to claim 1, wherein at least one of the radicals $R^1$ and $R^2$ stands for OH.
7. A process for preparing a complex compound according to claim 1, comprising reacting a compound of formula II

[Structure of formula II: flavone skeleton with substituents $R^1$ through $R^{10}$]

where $R^1$ to $R^{10}$ are as defined for the compound of formula I, with hydroxypropyl-gamma-cyclodextrin in a solution.
8. A process according to claim 7, wherein the hydroxypropyl-gamma-cyclodextrin is in excess or precisely in the molar ratio 1:1 or 2:1 relative to the compound of formula II.
9. A composition comprising a vehicle and 0.005 to 99% by weight of a complex compound according to claim 1.
10. A composition according to claim 9 wherein the compound of formula I is present in the composition in an amount of 0.01 to 20% by weight.
11. A composition, comprising a compound according to claim 1, and one or more UV filters.
12. A composition, comprising a compound according to claim 1, and one or more antioxidants.
13. A process for preparing a composition, comprising mixing a compound according to claim 1 with a cosmetically or dermatologically suitable vehicle.
14. A method or protection from light, comprising applying to the subject of protection from light a compound according to claim 1.
15. A method or filtering UV, comprising applying to the subject of protection from UV a compound according to claim 1.
16. A method of stabilizing a UV filter, comprising combining said UV filter with a compound of claim 1.
17. A compound according to claim 1, wherein $R^5$ stands for OH.
18. A compound according to claim 1, wherein $R^6$ stands for OH.
19. A compound according to claim 1, wherein each OR$^{11}$, independently of the others, stands for
OH,
a straight-chain or branched $C_1$- to $C_{20}$-alkoxy group,
a straight-chain or branched $C_3$- to $C_{20}$-alkenyloxy group,
a straight-chain or branched $C_1$- to $C_{20}$-hydroxyalkoxy group, where the hydroxyl group(s) may be bonded to a primary or secondary carbon atom in the chain and furthermore the alkyl chain may also be interrupted by oxygen, or a $C_3$- to $C_{10}$-cycloalkoxy group or $C_3$- to $C_{12}$-cycloalkenyloxy group, where the rings may each also be bridged by —$(CH_2)_n$— groups, where n=1 to 3.

20. A composition comprising a vehicle and 0.002 to 70% by weight of hydroxypropyl-gamma-cyclodextrin and 0.001 to 60% by weight of at least one compound of formula II

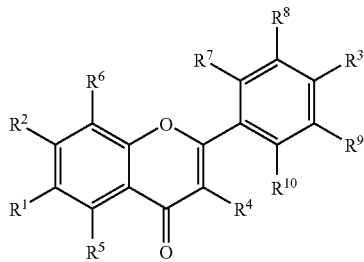

II where $R^1$ and $R^2$ are

H $OR^{11}$, where each $OR^{11}$, independently of the others, stands for

OH, a straight-chain or branched $C_1$- to $C_{20}$-alkoxy group, a straight-chain or branched $C_3$- to $C_{20}$-alkenyloxy group, a straight-chain or branched $C_1$- to $C_{20}$-hydroxyalkoxy group, where the hydroxyl group(s) may be bonded to a primary or secondary carbon atom in the chain and furthermore the alkyl chain may also be interrupted by oxygen, a $C_3$- to $C_{10}$-cycloalkoxy group or $C_3$- to $C_{12}$-cycloalkenyloxy group, where the rings may each also be bridged by —$(CH_2)_n$— groups, where n=1 to 3, or a mono- and/or oligoglycosyl radical, with the proviso that at least one radical from $R^1$ and $R^2$ stands for $OR^{11}$ and $R^3$ to $R^{10}$ may be identical or different and each stands, independently of one another, for

H, $OR^{11}$, a straight-chain or branched $C_1$- to $C_{20}$-alkyl group, a straight-chain or branched $C_3$- to $C_{20}$-alkenyl group, a straight-chain or branched $C_1$- to $C_{20}$-hydroxyalkyl group, where the hydroxyl group may be bonded to a primary or secondary carbon atom in the chain and furthermore the alkyl chain may also be interrupted by oxygen, or a $C_3$- to $C_{10}$-cycloalkyl group or $C_3$- to $C_{12}$-cycloalkenyl group, where the rings may each also be bridged by —$(CH_2)_n$— groups, where n=1 to 3.

21. A composition according to claim 20, which contains 0.01-20.0% by weight hydroxypropyl-gamma-cyclodextrin based on the total weight of the composition, and 0.01 to 20% by weight of a compound of formula II based on the composition as a whole.

* * * * *